United States Patent [19]

Reynoso et al.

[11] Patent Number: 5,827,515
[45] Date of Patent: Oct. 27, 1998

[54] *BACILLUS THURINGIENSIS* SPORULATION GENE

[75] Inventors: Mitra Shahabi Reynoso, San Jose; Sue S. Kalman, Saratoga; Nicole H. Cooper, San Jose; Takashi Yamamoto, Fremont, all of Calif.

[73] Assignee: Sandoz Ltd., Basel, Switzerland

[21] Appl. No.: 671,947

[22] Filed: Jul. 15, 1996

Related U.S. Application Data

[60] Provisional application No. 60/002,953 Aug. 30, 1995.
[51] Int. Cl.$^6$ .......................... A01N 63/00; C12N 15/00; C12N 1/20; C07H 21/04
[52] U.S. Cl. .................................. 424/93.2; 424/93.461; 424/405; 435/6; 435/69.1; 435/71.3; 435/172.1; 435/172.3; 435/252.31; 435/242; 435/320.1; 536/23.7; 536/23.71; 536/24.3
[58] Field of Search .................... 424/405, 93.2, 424/93.461; 435/69.1, 71.3, 172.1, 172.3, 242, 252.31, 320.1, 6; 530/350; 536/23.71, 23.7, 24.3

[56] References Cited

U.S. PATENT DOCUMENTS 5,277,906 1/1994 Zaehner et al. ........................... 424/93

OTHER PUBLICATIONS

Adams et al (1994) Molec. Micro 14:381–389 "Elucidation of the mechanism of cryIIIA over production in a mutagenized strain of *Bacillus thuringiensis* . . .".
Crickmore et al, (1990) Biochem. J 270:133–136 "The Construction of *Bacillus thuringiensis* strains expressing novel entomocidal δ–endotoxin combinations".
Foulger et al. (1991) Molec Micro 5:1363–1373 "Sequential activation of dual promoters by different sigma factors maintains SpoVJ expression . . .".
Lereclus et al. (1995) Bio/Technology 13:67–71 "Overproduction of encapsulated insecticical crystal proteins in a *Bacillus thuringiensis* . . .".

*Primary Examiner*—Robert A. Wax
*Assistant Examiner*—Lisa J. Hobbs
*Attorney, Agent, or Firm*—Larry W. Stults

[57] ABSTRACT

The present invention relates to a novel sporulation gene isolated from *B. thuringiensis*, and a DNA segment comprising the nucleic acid sequences encoding the gene and DNA sequences encoding crystal toxin proteins wherein said DNA segment is stably integrated into a *B. thuringiensis* host by homologous recombination. The invention further relates to a DNA segment wherein the sporulation gene is mutated thereby rendering an oligosporogenic or asporogenic transformed *B. thuringiensis* as a result of stable integration of the DNA segment into the *Bacillus thuringiensis* chromosome by homologous recombination.

38 Claims, 15 Drawing Sheets

FIGURE 1

```
1   MEQSMRKKNN NQINIVLNHR KKISLPAAEN KTVISNETAI KHEMLQRIEE
51  EMGKLVGMDD IKKIIKEIYA WIYVNKKRQE KGLKSEKQVL HMLFKGNPGT
101 GKTTVARMIG KLLFEMNILS KGHLVEAERA DLVGEYIGHT AQKTRDLIKK
151 AMGGILFIDE AYSLARGGEK DFGKEAIDTL VKHMEDKQHG FVLILAGYSR
201 EMNHFLSLNP GLQSRFPFII EFADYSVNQL LEIGKRMYED REYQLSKEAE
251 WKFRDHLHAV KYSSQITSFS NGRYVRNIVE KSIRTQAMRL LQEDAYDKND
301 LIGISSMDLM LEEETHST*
```

Sporulation gene interrupted with Tn917

ER=EcoRI
Kp=KpnI
Hd=HindIII
Bm=BamHI
Sm=SmaI
Sites in parenthesis were
eliminated during cloning.

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 1662 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 474..1427
        ( D ) OTHER INFORMATION: /codon_start= 474

( x i ) SEQUENCE DESCRIPTION: SEQ ID NO:1:

```
CAGGTGAAAT  GAAATCTTCG  TTACGAAGTG  TACGGTCTGG  TTGAATAGAT  ATCTCCATAT        60

TTTTCAATGG  ATTAGGAATG  TTTAGAAAAT  GATGCATTCT  ATTTAGTACA  ATAAATACAC       120

GATGCATCGT  TTTTTCTGAG  TAATGTCGAT  TCGTTTTAAA  TCGGAAAAGT  AATCTTCGTA       180

GTCTTTTGTA  CAAAGTGTAG  CCCATATATT  ACTGGAAGGG  AGCTTTTGT   TTTTTTCTAA       240

CCAATGTCCG  AAGTCTTCAA  CGTCATAAAC  ATAACGTTTA  ATAGTTGAGG  GTTTTCGGCC       300

TTTATTCAAT  AAAAAAATAG  AAAAGGCTTG  TATTGTATCA  TGGAATTCCG  TTGTCTCCAT       360

AGTCCCACCA  CCTTAATTAT  TTCTTATATT  ATAGCAAACT  TTTCTGAAAA  TAGGCATTTA       420

CAAGGGGGAC  AGGAATAATA  ATATTTGGTG  AGTGGATAAA  ATGAGGTGAT  TGT ATG          476
                                                              Met
                                                               1

GAA CAA TCG ATG CGA AAG AAA AAC AAC AAT CAA ATT AAT ATT GTG TTA              524
Glu Gln Ser Met Arg Lys Lys Asn Asn Asn Gln Ile Asn Ile Val Leu
              5                  10                  15

AAC CAT CGA AAG AAA ATT TCT TTG CCA GCC GCA GAA AAT AAA ACG GTA              572
Asn His Arg Lys Lys Ile Ser Leu Pro Ala Ala Glu Asn Lys Thr Val
         20                  25                  30

ATT TCA AAT GAA ACT GCA ATT AAA CAT GAA ATG CTG CAG AGA ATT GAA              620
Ile Ser Asn Glu Thr Ala Ile Lys His Glu Met Leu Gln Arg Ile Glu
     35                  40                  45

GAA GAG ATG GGG AAG CTT GTT GGG ATG GAT GAT ATA AAA AAG ATA ATA              668
Glu Glu Met Gly Lys Leu Val Gly Met Asp Asp Ile Lys Lys Ile Ile
 50                  55                  60                  65

AAA GAA ATA TAT GCT TGG ATT TAT GTG AAT AAA AAA AGA CAA GAG AAG              716
Lys Glu Ile Tyr Ala Trp Ile Tyr Val Asn Lys Lys Arg Gln Glu Lys
                     70                  75                  80

GGA TTG AAG TCA GAG AAG CAA GTA CTT CAT ATG CTG TTT AAA GGG AAT              764
Gly Leu Lys Ser Glu Lys Gln Val Leu His Met Leu Phe Lys Gly Asn
                 85                  90                  95

CCA GGT ACA GGG AAG ACA ACT GTT GCT AGA ATG ATA GGG AAA TTG CTG              812
Pro Gly Thr Gly Lys Thr Thr Val Ala Arg Met Ile Gly Lys Leu Leu
             100                 105                 110

TTT GAG ATG AAT ATT CTA TCG AAA GGC CAC TTG GTT GAA GCT GAA CGT              860
Phe Glu Met Asn Ile Leu Ser Lys Gly His Leu Val Glu Ala Glu Arg
         115                 120                 125

GCT GAT CTT GTA GGA GAG TAC ATC GGC CAT ACA GCT CAA AAA ACA AGA              908
```

-continued

| | | | | | | | | | | | | | | | | |
|---|---|---|---|---|---|---|---|---|---|---|---|---|---|---|---|---|
| Ala | Asp | Leu | Val | Gly | Glu | Tyr | Ile | Gly | His | Thr | Ala | Gln | Lys | Thr | Arg | |
| 130 | | | | 135 | | | | | 140 | | | | | 145 | | |

| GAC | TTA | ATA | AAA | AAA | GCA | ATG | GGA | GGT | ATT | TTG | TTT | ATT | GAT | GAG | GCG | 956 |
|---|---|---|---|---|---|---|---|---|---|---|---|---|---|---|---|---|
| Asp | Leu | Ile | Lys | Lys | Ala | Met | Gly | Gly | Ile | Leu | Phe | Ile | Asp | Glu | Ala | |
| | | | | 150 | | | | | 155 | | | | | 160 | | |

| TAT | TCT | TTA | GCT | CGA | GGA | GGA | GAG | AAG | GAC | TTT | GGA | AAA | GAA | GCA | ATT | 1004 |
|---|---|---|---|---|---|---|---|---|---|---|---|---|---|---|---|---|
| Tyr | Ser | Leu | Ala | Arg | Gly | Gly | Glu | Lys | Asp | Phe | Gly | Lys | Glu | Ala | Ile | |
| | | | 165 | | | | | 170 | | | | | 175 | | | |

| GAT | ACG | CTT | GTA | AAA | CAT | ATG | GAA | GAT | AAA | CAA | CAT | GGT | TTT | GTA | TTG | 1052 |
|---|---|---|---|---|---|---|---|---|---|---|---|---|---|---|---|---|
| Asp | Thr | Leu | Val | Lys | His | Met | Glu | Asp | Lys | Gln | His | Gly | Phe | Val | Leu | |
| | | 180 | | | | | 185 | | | | | 190 | | | | |

| ATT | TTA | GCT | GGA | TAT | TCA | AGA | GAG | ATG | AAT | CAC | TTT | CTT | TCA | TTA | AAT | 1100 |
|---|---|---|---|---|---|---|---|---|---|---|---|---|---|---|---|---|
| Ile | Leu | Ala | Gly | Tyr | Ser | Arg | Glu | Met | Asn | His | Phe | Leu | Ser | Leu | Asn | |
| 195 | | | | | 200 | | | | | 205 | | | | | | |

| CCA | GGG | CTG | CAA | TCT | CGT | TTT | CCA | TTT | ATT | ATT | GAA | TTT | GCG | GAT | TAC | 1148 |
|---|---|---|---|---|---|---|---|---|---|---|---|---|---|---|---|---|
| Pro | Gly | Leu | Gln | Ser | Arg | Phe | Pro | Phe | Ile | Ile | Glu | Phe | Ala | Asp | Tyr | |
| 210 | | | | | 215 | | | | | 220 | | | | | 225 | |

| TCG | GTA | AAT | CAG | TTG | TTG | GAA | ATT | GGG | AAA | AGA | ATG | TAT | GAA | GAT | CGT | 1196 |
|---|---|---|---|---|---|---|---|---|---|---|---|---|---|---|---|---|
| Ser | Val | Asn | Gln | Leu | Leu | Glu | Ile | Gly | Lys | Arg | Met | Tyr | Glu | Asp | Arg | |
| | | | | 230 | | | | | 235 | | | | | 240 | | |

| GAA | TAT | CAG | TTA | TCG | AAA | GAG | GCT | GAA | TGG | AAA | TTT | AGG | GAT | CAT | TTA | 1244 |
|---|---|---|---|---|---|---|---|---|---|---|---|---|---|---|---|---|
| Glu | Tyr | Gln | Leu | Ser | Lys | Glu | Ala | Glu | Trp | Lys | Phe | Arg | Asp | His | Leu | |
| | | | 245 | | | | | 250 | | | | | 255 | | | |

| CAT | GCT | GTA | AAG | TAT | TCG | TCG | CAA | ATT | ACA | TCG | TTT | AGT | AAT | GGG | CGG | 1292 |
|---|---|---|---|---|---|---|---|---|---|---|---|---|---|---|---|---|
| His | Ala | Val | Lys | Tyr | Ser | Ser | Gln | Ile | Thr | Ser | Phe | Ser | Asn | Gly | Arg | |
| | | 260 | | | | | 265 | | | | | 270 | | | | |

| TAT | GTA | CGG | AAT | ATT | GTT | GAA | AAA | TCA | ATT | CGT | ACA | CAG | GCG | ATG | CGG | 1340 |
|---|---|---|---|---|---|---|---|---|---|---|---|---|---|---|---|---|
| Tyr | Val | Arg | Asn | Ile | Val | Glu | Lys | Ser | Ile | Arg | Thr | Gln | Ala | Met | Arg | |
| | 275 | | | | | 280 | | | | | 285 | | | | | |

| TTG | TTG | CAA | GAA | GAT | GCC | TAT | GAT | AAA | AAT | GAT | TTA | ATT | GGA | ATA | TCG | 1388 |
|---|---|---|---|---|---|---|---|---|---|---|---|---|---|---|---|---|
| Leu | Leu | Gln | Glu | Asp | Ala | Tyr | Asp | Lys | Asn | Asp | Leu | Ile | Gly | Ile | Ser | |
| 290 | | | | | 295 | | | | | 300 | | | | | 305 | |

| AGT | ATG | GAT | TTG | ATG | CTC | GAA | GAG | GAG | ACG | CAC | AGT | ACA | TAAACTGTGC | 1437 |
|---|---|---|---|---|---|---|---|---|---|---|---|---|---|---|
| Ser | Met | Asp | Leu | Met | Leu | Glu | Glu | Glu | Thr | His | Ser | Thr | | |
| | | | | 310 | | | | | 315 | | | | | |

GTCGATTTTT GTGTATAAGT TCGTTTACTC TTTTTTTTCT TTTTCTTGGT GTACTTCATG 1497

GAAGTGTTCC ATTTTAGCGC TCTTTTCGTG TGCTGAATTA GGATCGTGTC CAAATTGATT 1557

TACTGAGCTT TTTTGAGCTC CTTTATTAAC GTGGTTTGTC ATTTGTATTC ACCTCACTTT 1617

AAAAATTAGT ATAAACATTA TATAAAGAAA AAATCGTTAG AAAGA 1662

( 2 ) INFORMATION FOR SEQ ID NO:2:

( i ) SEQUENCE CHARACTERISTICS:
        ( A ) LENGTH: 318 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Gln | Ser | Met | Arg | Lys | Lys | Asn | Asn | Asn | Gln | Ile | Asn | Ile | Val |
|---|---|---|---|---|---|---|---|---|---|---|---|---|---|---|---|
| 1 | | | | 5 | | | | | 10 | | | | | 15 | |

| Leu | Asn | His | Arg | Lys | Lys | Ile | Ser | Leu | Pro | Ala | Ala | Glu | Asn | Lys | Thr |
|---|---|---|---|---|---|---|---|---|---|---|---|---|---|---|---|
| | | | 20 | | | | | 25 | | | | | 30 | | |

| Val | Ile | Ser | Asn | Glu | Thr | Ala | Ile | Lys | His | Glu | Met | Leu | Gln | Arg | Ile |
|---|---|---|---|---|---|---|---|---|---|---|---|---|---|---|---|
| | | 35 | | | | | 40 | | | | | 45 | | | |

| Glu | Glu | Glu | Met | Gly | Lys | Leu | Val | Gly | Met | Asp | Asp | Ile | Lys | Lys | Ile |
|---|---|---|---|---|---|---|---|---|---|---|---|---|---|---|---|
| | 50 | | | | | 55 | | | | | 60 | | | | |

| Ile | Lys | Glu | Ile | Tyr | Ala | Trp | Ile | Tyr | Val | Asn | Lys | Lys | Arg | Gln | Glu |
|---|---|---|---|---|---|---|---|---|---|---|---|---|---|---|---|

-continued

```
         65                      70                      75                      80
Lys  Gly  Leu  Lys  Ser  Glu  Lys  Gln  Val  Leu  His  Met  Leu  Phe  Lys  Gly
                    85                      90                      95

Asn  Pro  Gly  Thr  Gly  Lys  Thr  Thr  Val  Ala  Arg  Met  Ile  Gly  Lys  Leu
              100                     105                     110

Leu  Phe  Glu  Met  Asn  Ile  Leu  Ser  Lys  Gly  His  Leu  Val  Glu  Ala  Glu
              115                     120                     125

Arg  Ala  Asp  Leu  Val  Gly  Glu  Tyr  Ile  Gly  His  Thr  Ala  Gln  Lys  Thr
     130                     135                     140

Arg  Asp  Leu  Ile  Lys  Lys  Ala  Met  Gly  Gly  Ile  Leu  Phe  Ile  Asp  Glu
145                     150                     155                     160

Ala  Tyr  Ser  Leu  Ala  Arg  Gly  Gly  Glu  Lys  Asp  Phe  Gly  Lys  Glu  Ala
                    165                     170                     175

Ile  Asp  Thr  Leu  Val  Lys  His  Met  Glu  Asp  Lys  Gln  His  Gly  Phe  Val
              180                     185                     190

Leu  Ile  Leu  Ala  Gly  Tyr  Ser  Arg  Glu  Met  Asn  His  Phe  Leu  Ser  Leu
              195                     200                     205

Asn  Pro  Gly  Leu  Gln  Ser  Arg  Phe  Pro  Phe  Ile  Ile  Glu  Phe  Ala  Asp
     210                     215                     220

Tyr  Ser  Val  Asn  Gln  Leu  Leu  Glu  Ile  Gly  Lys  Arg  Met  Tyr  Glu  Asp
225                     230                     235                     240

Arg  Glu  Tyr  Gln  Leu  Ser  Lys  Glu  Ala  Glu  Trp  Lys  Phe  Arg  Asp  His
                    245                     250                     255

Leu  His  Ala  Val  Lys  Tyr  Ser  Ser  Gln  Ile  Thr  Ser  Phe  Ser  Asn  Gly
              260                     265                     270

Arg  Tyr  Val  Arg  Asn  Ile  Val  Glu  Lys  Ser  Ile  Arg  Thr  Gln  Ala  Met
              275                     280                     285

Arg  Leu  Leu  Gln  Glu  Asp  Ala  Tyr  Asp  Lys  Asn  Asp  Leu  Ile  Gly  Ile
     290                     295                     300

Ser  Ser  Met  Asp  Leu  Met  Leu  Glu  Glu  Glu  Thr  His  Ser  Thr
305                     310                     315
```

(2) INFORMATION FOR SEQ ID NO:3:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

GGCTTTCGCT ACCTGGAGAG ACGCGCCCGC      30

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO ( x i ) SEQUENCE DESCRIPTION: SEQ ID NO:4:

CCAGACCAAC TGGTAATGGT AGCGACCGGC     30

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

GAGAGATGTC ACCGTCAAG     19

( 2 ) INFORMATION FOR SEQ ID NO:6:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

CCCTGTACCT GGATTCCC     18

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

GGGAATCCAG GTACAGGG     18

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

CCATCCCAAC AAGCTTCCC     19

( 2 ) INFORMATION FOR SEQ ID NO:9:

( i ) SEQUENCE CHARACTERISTICS:
           ( A ) LENGTH: 19 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GGGAAGCTTG TTGGGATGG                                            19

( 2 ) INFORMATION FOR SEQ ID NO:10:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CCTGTCCCCC TTGTAAATGC                                         20

( 2 ) INFORMATION FOR SEQ ID NO:11:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

GCATTTACAA GGGGGACAGG                                         20

( 2 ) INFORMATION FOR SEQ ID NO:12:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

CGCCGTCTAC TTACAAGCAG C                                        21

( 2 ) INFORMATION FOR SEQ ID NO:13:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

GGTGGTGGGA CTATGGAG                                        18

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

CTCCATAGTC CCACCACC                                        18

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:

CGAGGAGGAG AGAAGGAC                                        18

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

GTCCTTCTCT CCTCCTC                                         17

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:

CACGATGCAT CG 12

( 2 ) INFORMATION FOR SEQ ID NO:18:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:18:

CACGATGCAT CG 12

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:19:

CGAAAGAGGC TGAATGG 17

( 2 ) INFORMATION FOR SEQ ID NO:20:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:20:

GGGCGGTATG TACGG 15

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (xi) SEQUENCE DESCRIPTION: SEQ ID NO:21:

CCGTACATAC CGCCC 15

(2) INFORMATION FOR SEQ ID NO:22:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:22:

GCATCAAATC CATACTCGAT ATTCC 25

(2) INFORMATION FOR SEQ ID NO:23:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:23:

CGAGTATGGA TTTGATGCTC G 21

(2) INFORMATION FOR SEQ ID NO:24:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:24:

GGACACGATC CTAATTCAGC 20

(2) INFORMATION FOR SEQ ID NO:25:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO ( x i ) SEQUENCE DESCRIPTION: SEQ ID NO:25:

GCTGAATTAG GATCGTGTCC 20

( 2 ) INFORMATION FOR SEQ ID NO:26:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:26:

GATGTGATTG TAAGGAACAA TCGAAGCGAT AGAAAAAC 38

( 2 ) INFORMATION FOR SEQ ID NO:27:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:27:

GATCTTGTAT GAGAGTAAAT CGGCCATACA GC 32

( 2 ) INFORMATION FOR SEQ ID NO:28:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:28:

GCTGTATGGC CGATTTACTC TCATACAAGC TC 32

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:29:

CTATACAGCA TGTTAATGAT CCC 23

( 2 ) INFORMATION FOR SEQ ID NO:30:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:30:

AGCTTGCGGC CGCGTCGACC CCGGGCCATG GGGGCCCG    38

( 2 ) INFORMATION FOR SEQ ID NO:31:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:31:

AATTCGGGCC CCCATGGCCC GGGGTCGACG CGGCCGCA    38

( 2 ) INFORMATION FOR SEQ ID NO:32:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:32:

GCGAAAGAAA AACAACAATC    20

( 2 ) INFORMATION FOR SEQ ID NO:33:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:33:

GGAACGCTAC ATACTAGTGA TAGAGTAG    28

( 2 ) INFORMATION FOR SEQ ID NO:34:

( i ) SEQUENCE CHARACTERISTICS:

(A) LENGTH: 28 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GCTTGTACAC CGCAACTGTT TTCGCATG                                                         28

(2) INFORMATION FOR SEQ ID NO:35:

(i) SEQUENCE CHARACTERISTICS:
                (A) LENGTH: 20 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

GAAATCGGCT CAGGAAAAGG                                                                  20

(2) INFORMATION FOR SEQ ID NO:36:

(i) SEQUENCE CHARACTERISTICS:
                (A) LENGTH: 19 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:36:

AGCAAACCCG TATTCCACG                                                                   19

(2) INFORMATION FOR SEQ ID NO:37:

(i) SEQUENCE CHARACTERISTICS:
                (A) LENGTH: 18 base pairs
                (B) TYPE: nucleic acid
                (C) STRANDEDNESS: single
                (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:37:

GCACGATCAT GCGCACCC                                                                    18

BACILLUS THURINGIENSIS SPORULATION GENE

PRIOR RELATED APPLICATIONS

This application claims priority under 35 U.S.C. § 119(e) to U.S. Provisional application Ser. No. 60/002,953, filed Aug. 30, 1995.

BACKGROUND OF THE INVENTION

It is well known that *Bacillus thuringiensis*, which accounts for the majority of all biopesticides used today, produces a crystalline inclusion during sporulation, and it is this crystalline inclusion which is composed of one or more δ-endotoxins and is responsible for toxicity to a wide range of insect hosts including larvae of lepidopteran, coleopteran, and dipteran insects.

Due to considerable interest in the use of *B. thuringiensis* as a biological pesticide, numerous studies have been done on identification of the insecticidal proteins and genes encoding these proteins in *B. thuringiensis* strains. However, less is known about the genes involved in the sporulation pathway. The sporulation genes are not only responsible for sporulation but also are associated with crystal production. Most insecticidal crystal proteins are expressed only during sporulation. Therefore, the identification and characterization of the genes involved in the sporulation pathway would enhance our knowledge and ability to manipulate crystal production and the sporulation cycle, and further would potentially increase the effectiveness of *B. thuringiensis* as a biological pesticide.

The production of viable spores by recombinant *B. thuringiensis* strains can be a disadvantage with respect to the use of *B. thuringiensis* products. All commercial *B. thuringiensis* strains form spores which are released into the surrounding environment in combination with the insecticidal proteins and while the spores may provide some insecticidal advantage, they are highly durable structures and can survive in the soil under extreme weather conditions.

The use of asporogenic or oligosporogenic *B. thuringiensis* in biopesticides could prevent or diminish the release of these viable spores making the use of *B. thuringiensis* biopesticides an even more attractive alternative to the use of conventional pesticides. Moreover, documentation in the literature suggests that over expression of certain cry genes can occur in asporogenic strains. For example, expression of the cryIIIA gene has been observed to increase in sporulation mutants of Bacillus strains.

The morphological and physiological changes that occur during sporulation have been studied extensively in *Bacillus subtilis*. In general once sporulation is initiated, the cells undergo a number of morphological stages and sporulation involves a radical change of the biosynthetic activity of the bacterium. As sporulation begins, the chromosome condenses. At stage II, cell division occurs producing sister cells that are different in size. The smaller cell is the daughter cell, also known as the forespore or prespore. The larger cell is designated the mother cell. During stage III, the mother cell engulfs the forespore resulting in the formation of a double-membrane around the forespore inside the mother cell. A modified form of a cell wall known as cortex is synthesized between the inner and outer membranes of the prespore during stage IV followed by spore coat deposition on the outer membrane of the prespore during stage V. Stage VI is defined as the complete maturation of the spore. At this stage the spore develops its characteristic properties of resistance to radiation, heat, lysozyme, and organic solvents. Finally, the mother cell lyses and the mature spore is released in stage VII. The free spore is refractile and can be easily observed using light microscopy.

Genes that are needed for sporulation can be recognized by creating mutations which permit normal vegetative growth, but block sporulation. In *Bacillus subtilis* at least 100 sporulation genes have been identified which are involved in the sporulation process. The genes are designated as spo0, spoII, spoIII, etc. depending upon the stage in which sporulation is blocked. Genes involved in later events of sporulation in *Bacillus subtilis* have been identified as spoV genes and spoV A, B, D, Ea, Eb, G, Id, J and R have been identified in databases. The capital letters indicate loci containing mutations conferring similar phenotypes but mapping at distinct chromosomal positions. Sporulation and gene expression and control in *Bacillus subtilis* is further discussed in Errington, Jeffrey, *Bacillus substilis* Sporulation: Regulation of Gene Expression and Control of Morphogenesis, Microbio. Rev. 57 (1–33), which is hereby incorporated by reference.

The present invention is the first known isolation of a stage V sporulation gene from a host *B. thuringiensis* strain. The present gene designated spoVBt1 is about 65.5% homologous to the *B. subtilis* spoVJ gene at the nucleotide level and, the transposon, Tn917 was used as a tool for the identification of spoVBt1.

The novel spoVBt1 gene and related spoV DNA sequences (as defined below) are used in a method of stably introducing exogenous DNA into bacteria. The spoV sequences of the invention are substantially homologous to a fragment of a sporulation gene located on a bacterial chromosome. The bacterial fragment comprising a sporulation gene serves as a site for chromosomal integration of the exogenous DNA and spoV sequence.

Surprisingly it has also been found that if the spoVBt1 gene and other spoV DNA sequences are mutated by, for example, point mutations not only will exogenous DNA be incorporated into the bacterial chromosome but also the recipient bacteria will form mutated spores.

SUMMARY OF THE INVENTION

The present invention relates to an isolated spoVBt1 gene having the nucleotide sequence as shown in SEQ. ID NO.1. This invention further relates to an isolated spoV DNA sequence selected from the group consisting of i) the above-identified isolated spoVBt1 gene; ii) a nucleotide sequence encoding a *Bacillus thuringiensis* sporulation protein as depicted in SEQ. ID NO:2; iii) a nucleotide sequence encoding a *Bacillus thuringiensis* sporulation protein substantially similar to the protein depicted in SEQ. ID NO:2; iv) a nucleotide sequence which hybridizes to a complementary strand of a sequence of i), ii) or iii), under stringent hybridization conditions and v) a truncated nucleotide sequence of i), ii), iii) or iv) above wherein said truncated sequence includes at least 300 nucleotides and more preferably at least 500 nucleotides.

The invention further relates to a DNA segment comprising the spoV DNA sequence defined above linked to a DNA sequence encoding at least one insecticidal crystal protein wherein codons of said spoV DNA sequence comprises nucleotide sequences substantially homologous to sequences present in *Bacillus thuringiensis* chromosomal DNA and which allows for recombination. This DNA segment may be chromosomally integrated into a host *Bacillus thuringiensis*. The *B. thuringiensis* chromosomal fragment which is substantially homologous to the spoV DNA sequence serves as an integration site for the DNA segment. In this manner the invention includes an increase in the crystal gene content of a bacterium.

The invention also comprises a DNA segment comprising a mutated spoV DNA sequence (defined herein below) operably linked to a DNA sequence encoding at least one insecticidal crystal toxin protein wherein codons of said mutated spoV DNA sequence comprise nucleotide sequences substantially homologous to sporulation gene sequences present in *Bacillus thuringiensis* chromosomal DNA so that the DNA segment is capable of being inserted into the bacterial chromosomal sporulation gene locus and replicated and further the insecticidal crystal toxin protein is capable of being expressed in a Bacillus host wherein said host is rendered asporogenic or oligosporogenic.

The invention has particular relevance to recombinant *B. thuringiensis* strains wherein toxic crystal proteins are expressed by a transformed host but wherein spores are released into the environment. Therefore, in addition, the invention concerns a method of preparing asporogenic or oligosporogenic insecticidal crystal protein producing *Bacillus thuringiensis* strains comprising a) obtaining a DNA segment which includes a mutated spoV DNA sequence operably linked to at least one and no more than three insecticidal crystal protein encoding sequences; b) introducing said segment into a *Bacillus thuringiensis* host capable of sporulation; c) allowing homologous recombination to occur between the DNA segment and a substantially homologous nucleotide fragment of a sporulation gene in the host *Bacillus thuringiensis* chromosome wherein said DNA segment is stably integrated into the *Bacillus thuringiensis* chromosome and disrupts the sporulation process and; d) isolating a stably transformed asporogenic or oligosporogenic *Bacillus thuringiensis* host transformant wherein said stably transformed host is capable of expressing the introduced insecticidal crystal protein sequences.

A further object of the invention includes the transduction of a transformed *Bacillus thuringiensis* host comprising exposing the transformed host to a transducing phage; allowing said phage to replicate in said host wherein one to three exogenous insecticidal crystal protein encoding DNA sequences integrated into said *Bacillus thuringiensis* host chromosome are incorporated into the phage and introducing the insecticidal crystal protein encoding DNA sequence from said phage into a recipient *Bacillus thuringiensis* wherein said introduced exogenous crystal protein encoding DNA sequence is stably incorporated into said chromosome of the recipient and expressed in said recipient. The recipient *Bacillus thuringiensis* may or may not be rendered asporogenic or oligosporogenic depending on the DNA segment.

In this regard the invention includes a method of using a *Bacillus thuringiensis* chromosomal sporulation gene fragment as a locus for chromosomal integration of a DNA segment, the DNA segment comprising at least one insecticidal crystal protein encoding gene wherein said gene is stably integrated into the *Bacillus thuringiensis* chromosome.

The invention further relates to a broad spectrum insecticidal composition comprising an insecticidally effective amount of a transformed *B. thuringiensis* according to the invention and an acceptable carrier thereof.

Another objective of the present invention is the genetic engineering of a *B. thuringiensis* host whereby use of said host for the control of pathogenic insects provides an environmentally safer biopesticide wherein viable spores are not released into the environment.

A further object of the invention includes a method of protecting crop plants comprising applying to the locus where control is desired a composition of the invention.

Other aspects of the present invention will become apparent to those skilled in the art from the following description and figures.

BRIEF DESCRIPTION OF THE FIGURES

FIG. 1 illustrates the predicted amino acid sequence of the isolated spoVBt1 gene as illustrated in SEQ ID NO.1 and corresponds to SEQ. ID NO.2.

DETAILED DESCRIPTION OF THE INVENTION

Figure 2:
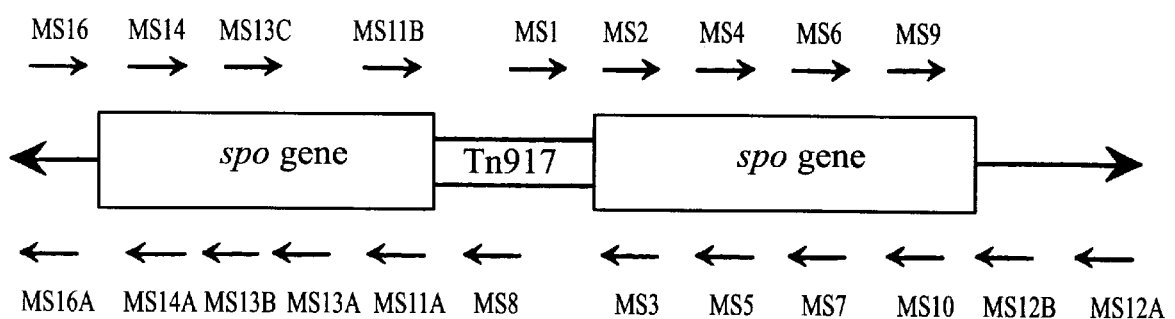
FIG. 2 illustrates the spoVBt1 gene interrupted with Tn917 and the location of oligonucleotides used for sequencing.

The isolation and purification of a sporulation gene from *B. thuringiensis* HD1Mit9::Tn917 is described at length in Example 1. The nucleotide sequence is shown in SEQ. ID NO.1. The molecular weight of the putative protein product is calculated as 36.7 kDa. The sporulation gene is designated spoVBt1. The predicted amino acid sequence is shown under the nucleotide sequence. The putative ribosome binding site includes nucleotides 459 through 470 of SEQ ID NO.1 and the predicted transcription terminator stemloop includes nucleotides 1415 through 1424 and 1431 through 1440.

The invention also includes those nucleotide sequences which encode the protein of SEQ. ID NO.2. It will be appreciated by those skilled in the art that an amino acid is frequently encoded by two or more codons, for example the amino acid leucine is encoded by the nucleic acid sequences of the following codons, TTA, TTG, CTT, CTA, CTG and CTC. Codons which code for the same amino acid are considered synonymous codons.

The invention still further embodies nucleotide sequences which encode sporulation proteins that are substantially similar to the protein depicted in SEQ. ID NO.2. The term substantially similar to the protein depicted in SEQ. ID NO.2 means that the proteins are stage V sporulation proteins and the degree of similarity of the amino acid sequences is preferred to be at least 80%, more preferred the degree of similarity is at least 85%, and most preferred the degree of similarity is 95% to SEQ. ID No:2. A nucleotide sequence encoding a stage V sporulation gene includes those genes involved in late events of the sporulation process. For example those genes involved in deposition of spore coat protein, development of germination processes and progressive acquisition of resistance to organic solvent, heat and lysozyme to name a few.

In the context of the present invention, two amino acids sequences with at least 85% similarity to each other have at least 85% identical or conservatively replaced amino acid residues.

For the purpose of the present invention conservative replacements may be made between amino acids within the following groups: (i) alanine, serine and threonine; (ii) glutamic acid and aspartic acid; (iii) arginine and lysine; (iv) asparagine and glutamine; (v) isoleucine, leucine, valine and methionine; and (vi) phenylalanine, tyrosine and tryptophan.

The invention still further includes nucleic acid sequences which are complementary to one which hybridizes under stringent conditions with any of the above disclosed nucleic acid sequences. A first nucleotide sequence which "hybridizes under stringent hybrization conditions" to a second nucleotide sequence can not be substantially separated from the second sequence when the second sequence has been bound to a support and the first and second sequences have been incubated together at 65° C. in 2× standard saline citrate containing 0.1% (w/v) sodium dodecyl sulphate, the thus hybridized sequences then being washed at 50° C. with 0.5× standard saline citrate containing 0.1% (w/v) sodium dodecyl sulphate.

Specifically, the spoVBt1 gene depicted in SEQ. ID NO.1 is a gene that is associated with later stages of the sporulation process. In this regard the nucleotide sequences of the invention are referred to under the general heading of spoV DNA sequences and more specifically are identified as i) a spoVBt1 gene having the nucleotide sequence shown in SEQ. ID NO.1; ii) a nucleotide sequence encoding a *Bacillus thuringiensis* sporulation protein as depicted in SEQ. ID NO.2; iii) a nucleotide sequence encoding a *Bacillus thuringiensis* sporulation protein substantially similar to the protein depicted in SEQ. ID NO.2; iv) a nucleotide sequence which hybridizes to a complementary strand of i), ii) or iii) under stringent hybridization conditions; and v) a truncated nucleotide sequence of i), ii), iii) or iv) above wherein the truncated sequence includes at least 300 nucleotides and more preferably at least 500 nucleotides.

While a truncated spoV DNA sequence is most preferably at least 500 nucleotides, a particularly preferred sequence is base pair 488 to 1404, inclusive, of SEQ ID NO.1. This particular sequence is referred to herein as (t)spoVBt1-1.

Accordingly, the invention provides, a DNA segment comprising a spoV DNA sequence as defined above or a mutated spoV DNA sequence as defined herein below operably linked to other DNA sequences wherein the DNA sequences encode exogenous or foreign proteins. For example in a preferred embodiment the DNA segment may include in addition to the spoV DNA sequence, insecticidal crystal protein encoding DNA sequences. Preferably, the DNA segment will include one to three insecticidal protein encoding genes. Such sequences include but are not limited to cryIA(a), cryIA(b), cryIA(c), cryIB, cryIC, cryIC(b), cryID, cryIE, cryIF, cryIG, cryIH, cryIIA, cryIIB, cryIIIA, cryIIIB, cryIIIC, cryIVA, cryIVB, cryIVC, cryID, cryV genes, mixtures thereof and sequences constructed from parts of these cry genes. In particular, the crystal protein encoding DNA sequences include cryIA(b), cryIA(c), cryIC, cryIIA, and cryIE. Sequences constructed from parts of any genes include hybrid crystal encoding proteins wherein domains of two or three different crystal encoding toxins are included. These hybrid genes are known in the art and may include for example domain I and domain II of one crystal encoding gene and domain III of another crystal toxin encoding gene. In particular, domain III of cryIC is preferred. The hybrid G27 is one such example wherein the gene includes domain I and II of cryIE and domain III of cryIC. The protein G27 is further described in Bosch et al., Biotechnology 12:9 5–918 (1994) the contents of which are hereby incorporated by reference. However, one skilled in the art can envisage various combinations of toxins comprising a hybrid toxin encoding gene and these combinations are incorporated into the invention. The terms foreign or exogenous protein or gene are terms used in the art to denote a gene which has been transferred to a host cell from a source other than the host cell.

According to this invention, the most preferred hosts include *B. thuringiensis* subspecies, and particularly subspecies thuringiensis, kurstaki, dendrolimus, galleriae, entomocidus, aizawai, morrisoni, tolworthi and israelensis, and most particularly *B. thuringiensis kurstaki*.

The DNA segment may further comprise an origin of replication for a gram-negative bacterium. Any origin of replication capable of functioning in one or more gram negative bacterial species or strains of Enterobacter, Nitrosomonas, Pseudomonas, Serratia, Rhizobium, and Azotobacter genera among others may be used. After cloning the DNA segment in a gram-negative bacterium such as *E. Coli* and transforming a *Bacillus thuringiensis*, the only remaining exogenous insecticidal DNA sequences will be those integrated into the host's chromosome. Since the gram negative origin of replication will not function in a *Bacillus thuringiensis* host, a host transformed with the DNA segment will neither replicate nor express the crystal toxin encoding genes unless the DNA segment becomes integrated into the host chromosome.

The DNA segment may further comprise other nucleic acid sequences including selectable markers. In general, selectable markers for drug resistance, chemical resistance, amino acid auxotrophy or prototrophy or other phenotypic variations useful in the selection or detection of mutant or recombinant organisms can be used.

Other sequences may also be incorporated into the DNA segment including but not limited to regulatory sequences capable of directing transcription and translation of the crystal toxin encoding sequences within the host cell, such as promoters, operators, repressors, enhancer sequences, ribosome binding sites, transcription initiation and termination sites and the like. Specific examples include the CryIC promoter, CryIA(c) terminator and ermC promoter. Additionally, sequences adjacent to the claimed spoVBt1 gene may be included. These sequences comprise promoter sequences, downstream enhancer sequences and the like.

The spoV DNA sequence suitable for use in the invention is substantially homologous to a nucleotide fragment of the *B. thuringiensis* chromosome. This fragment will generally be part of a sporulation gene and it serves as an integration site for the DNA segment of the invention into the host DNA by homologous recombination thereof with the bacterial DNA. The DNA segment of the invention may be provided as either a circular, closed DNA segment wherein homologous recombination occurs by means of a single cross over event or as a linear DNA segment wherein homologous recombination occurs by means of a double-cross over event. Thus the substantially homologous DNA sequences may be as one or two flanking DNA sequences. The spoV DNA sequences are homologous to a fragment of the bacterial chromosome in the range of about 15–1600 nucleotide bases and more preferably 200–1200. One skilled in the art will also recognize that at the integration site, multiple insertions can occur.

The term homologous as used herein in the context of nucleotide sequences means the degree of similarity between the sequences in different nucleotide molecules. Therefore two nucleic acid molecules which are 100% homologous have identical sequences of nucleotides. A substantially homologous nucleotide sequence or fragment is one wherein the sequences of the fragment are at least 90% and preferably 95% identical. Homologous recombination is defined as general recombination which occurs between two sequences which have fairly extensive regions of homology; the sequences may be in different molecules.

The DNA segment of the invention may be carried on a phage or a vector, a preferred vector is a plasmid and in particular the plasmids disclosed herein and in PCT International application WO 9425611, published Mar. 19, 1995 which is hereby incorporated by reference in its entirety. Additionally, the DNA segment may be carried on a hybrid shuttle vector for gram-positive bacteria. Appropriate vectors include any vector capable of self-replication in gram-negative bacteria, yeast's or any monocellular host in addition to gram-positive bacteria. Such shuttle vectors are known in the art.

Transformation, the process in which exogenous DNA is taken up by a recipient *B. thuringiensis* may be conducted by techniques known in the art and includes transfection, electro-poration, transduction, or conjugation. Particularly preferred methods include electro-poration and transduction. Host isolation may be conducted by selecting from the selectable marker on the transformed host. Transformed host may then be amplified by known techniques.

Therefore a preferred embodiment of the present invention is a method of preparing a transformed *Bacillus thuringiensis* host expressing exogenous insecticidal crystal protein proteins comprising a) obtaining a DNA segment comprising
   1) an origin of replication from a gram negative bacterium;
   2) a spoV DNA sequence selected from the group consisting of
     i) a spoVBt1 gene having the nucleotide sequence show in SEQ. ID NO.1;
     ii) a nucleotide sequence encoding the protein depicted in SEQ. ID NO.2,
     iii) a nucleotide sequence encoding a *Bacillus thuringiensis* sporulation protein substantially similar to the protein depicted in SEQ. ID NO.2;
     iv) a nucleotide sequence which hybridizes to a complementary strand of i), ii) or iii) under stringent hybridization conditions; and
     v) a truncated nucleotide sequence of i), ii) or iv) above wherein the truncated sequence includes at least 300 nucleotides and
   3) a DNA sequence encoding one to three insecticidal crystal proteins;
b) introducing said segment into a *Bacillus thuringiensis* host;
c) allowing homologous recombination between the DNA segment and a substantially homologous nucleotide fragment of a sporulation gene in the host *Bacillus thuringiensis* chromosome wherein the DNA segment is stably integrated into the *Bacillus thuringiensis* host chromosome; and
d) isolating stably transformed *Bacillus thuringiensis* transformants wherein said stable transformed *Bacillus thuringiensis* is capable of producing the exogenous insecticidal crystal proteins.

Also included in the invention is the transformed Bacillus host and progeny thereof formed by amplification of said transformant.

Mutation of a sporulation gene or genes may cause the formation of mutant spores. Mutant spores as used herein include spores from oligosporogenic and asporogenic strains. Asporogenic *B. thuringiensis* strains are those wherein spores are not formed because the strain is not capable of forming spores. Alternatively, oligosporogenic *B. thuringiensis* strains are those wherein spores are formed however, the spores may not be viable for a variety of reasons or the spores are viable but they are sensitive to heat, cold or organic solvents and rendered nonviable upon exposure thereto. Frequently, oligosporogenic *B. thuringiensis* produce what is known in the art as phase grey spores.

Mutation of a gene may occur in a number of ways well known to those in the art and include chemical mutagenesis, point mutations, deletions, insertional mutations, including use of transposons, and the like.

One embodiment of the present invention is a method of using a DNA segment of the invention in a manner to interrupt the chromosomal DNA encoding for sporulation genes. In this respect the DNA segment includes a mutated spoV DNA sequence.

A mutated spoV DNA sequence is a spoV DNA sequence of the invention wherein the sequence is altered with point mutations, deletions, or inserts. Point mutations are generally understood to mean any mutation involving a single nucleotide including the gain or loss of a nucleotide resulting in a frame shift mutation as well as transition and transversion mutations. The point mutations can occur at various codons. Preferred point mutations are used to create stop codons and may be used to destroy the ribosome binding site and methionine start codons. These stop codons can occur anywhere throughout the gene, however, they do not interrupt the process of homologous recombination between the DNA segment according to the invention and the substantially homologous chromosomal sporulation gene locus.

A mutated spoV DNA sequence may include 1 to about 25 stop codons although either a greater number than 25 or less than 25 can be used. A specific mutated spoV DNA sequence of the invention is part of the spoVBt1 sequence of SEQ. ID NO.1 including nucleotide sequence 465 to 1256 inclusive wherein the following nucleotides as illustrated in Table 1 have been altered. In general, stop codons should be engineered before nucleotide 1404 of SEQ ID No.1, or a related spoV DNA sequence to prevent reversion to wild type spores in the recipient host cells. Additionally, the peptide encoded by a mutated spoV DNA sequence should be less than 306 amino acids. Most preferably stop codons should be engineered before nucleotide 1256 of SEQ ID No.1 or a related spoV DNA sequence.

TABLE 1

| Nucleotide # | original codon | altered to |
|---|---|---|
| 465 | G | T |
| 475 | T | A |
| 487 | T | A |
| 492 | A | T |
| 873 | G | T |
| 881 | C | A |
| 1243 | T | A |
| 1254 | A | T |

This specific mutated spoV DNA sequence is designed (m) spoVBt1-8.

A mutated spoV DNA sequence may include the point mutations described above or a sequence substantially homologous to the non-mutated codons of sequence 465 to 1254.

The mutated spoV DNA sequence also includes a spoV DNA sequence which has exogenous inserts of nucleic acid sequences for example, the inserts may comprise 2 to 15 nucleotides; however, more nucleotides could be used.

Therefore another preferred embodiment of the present invention is a method of preparing a transformed oligosporogenic or asporogenic *Bacillus thuringiensis* host expressing one to three exogenous insecticidal crystal proteins comprising a) obtaining a DNA segment comprising
1) an origin of replication from a gram negative bacterium;
2) a mutated spoV DNA sequence selected from the group consisting of
   i) a spoVBt1 gene having the nucleotide sequence show in SEQ. ID NO.1;
   ii) a nucleotide sequence encoding the protein depicted in SEQ. ID NO.2;
   iii) a nucleotide sequence encoding a sporulation protein substantially similar to the protein depicted in SEQ. ID NO:2;
   iv) a nucleotide sequence which hybridizes to a complementary strand of i), ii) and iii) under stringent hybridization conditions; and
   v) a truncated nucleotide sequence of i), ii), iii) or iv) above wherein said truncated sequence includes at least 300 nucleotides;
wherein the nucleotide sequence of i), ii), iii), iv) or v) above has one or more point mutations, inserts or deletions; and
3) a DNA sequence encoding one to three insecticidal crystal toxin proteins;
b) introducing said segment into a sporulating *Bacillus thuringiensis* host;
c) allowing homologous recombination between the DNA segment and a substantially homologous sporulation gene fragment of the host *Bacillus thuringiensis* chromosome wherein the DNA segment including the mutated spoV DNA sequence is stably integrated into the *Bacillus thuringiensis* host chromosome; and
d) isolating stably transformed *Bacillus thuringiensis* transformants wherein said stable transformed *Bacillus thuringiensis* is capable of producing the exogenous crystal toxin and is oligosporogenic or asporogenic.

The method further comprises employing the transformed aligosporogenic or asporogenic host.

Transduction is a virus mediated transfer of host DNA from one host cell (a donor) to another cell (recipient). When a phage replicates in a donor cell, a few progeny virions encapsidate pieces of the host DNA in addition to phage DNA. These virions can adsorb to a new host cell and introduce their DNA in the usual way. In this invention, the host strain which is transformed with a DNA segment of the invention can be further transduced with a phage. The host (donor) DNA which is incorporated into the phage undergo recombination with a homologous region of a recipient's chromosome so that the genes can be stably inherited. This is generally referred to by those skilled in the art as generalized transduction. Phages are known by those skilled in the art and include all phages capable of infecting *B. thuringiensis* strains, for example CP-51 and CP-51ts45 and all derivations thereof. In the present invention, the preferred recipient call is from a strain of *Bt kurstaki*.

Therefore, in another aspect the invention is a method of transducing a transformed *Bacillus thuringiensis* comprising a) exposing a *Bacillus thuringiensis* host of the invention to a transducing phage;
b) allowing the phage to replicate in the host wherein one to three exogenous crystal protein encoding genes integrated into the host chromosome are incorporated into the phage; and
c) introducing the exogenous crystal protein encoding sequences from the phage into a recipient *Bacillus thuringiensis* strain wherein said introduced exogenous crystal protein encoding sequences are stably incorporated into the recipient *Bacillus thuringiensis* chromosome and expressed in said recipient.

The recipient *Bacillus thuringiensis* may be rendered oligosporogenic or asorogenic depending on the spoV DNA sequence used in the DNA segment introduced into the transformed host. A most preferred locus for chromosomal integration is the spoVBt1 nucleotide fragment of the recipient *Bacillus thuringiensis* strain. However, other sporulation gene fragments may equally serve as a chromosomal locus. Preferred sporulation gene fragments include those substantially homologous with a spoV DNA sequence.

The stable incorporation of the DNA segment according to the invention into a host chromosome is defined as the maintenance of the DNA segment within the host chromosome through many generations.

The invention further relates to pesticidal compositions wherein the transformed *Bacillus thuringiensis* or protein derived from said Bacillus are the active ingredient. The compositions of the invention include an asporogenic or oligosporogenic *Bacillus thuringiensis* encoding one or more insecticidal Cry proteins and is applied at an insecticidally effective amount. An insecticidally effective amount is defined as the amount of an active ingredient which causes substantial mortality of an insect to be controlled and the amount will vary depending on such factors as the specific Cry protein, specific insects to be controlled, the specific plant to be treated, and the method of applying the insecticidally active compositions.

The compositions of the invention may contain about $10^6$ to about $10^{13}$ microorganisms per gram ca. The pesticidal concentration will vary depending on the carrier of the particular formulation. The compositions contain from 0.1 to 99% of the transformed host or progeny thereof and 0 to 99.9% of a solid or liquid carrier.

The insecticidal compositions of the invention may be formulated with an agriculturally acceptable carrier. The formulated compositions may be in the form of dusts, granular material, suspensions in oil or water, emulsions or as wettable powders. Suitable agricultural carriers may be solid or liquids and are well known to those in the art. Agriculturally acceptable carriers as used herein include all adjuvants such as wetting agents, spreaders, emulsifiers, dispersing agents, foaming agents foam, suppressants, pentrants, surfactants, solvents, solublizers, buffering agents, stickers etc., that are ordinarily used in insecticide formulation technology. These are well known to those skilled in the art of insecticide formulation.

The formulations comprising the asporogenic or oligosporogenic *Bacillus thuringiensis* strains and one or more liquid or solid adjuvants are prepared in a manner known to those in the art.

The compositions of this invention are applied to the locus where control is desired and typically onto the foliage of a plant to be protected by conventional methods. These application procedures are well known in the art. The formulations of the present composition may be applied by spreading about $10^8$ to about $10^{16}$ spores per acre. With oligosporogenic or asporogenic compositions the spores may be present but are either immature or non- viable. The compositions are best applied as sprays to plants with subsequent reapplication. Plants to be protected within the scope of the invention include but are not limited to cereals, fruits, leguminous plants, oil plants, vegetable plants, deciduous and conifer trees, beet plants, ornamentals. The compositions may be effective against pests of the orders Coleoptera, Lepidoptera and Diptera.

The methods of the present invention make use of techniques of genetic engineering and molecular cloning that are known to those skilled in the art using commercially available equipment and are included in Maniatis, et al. Molecular Cloning: A Laboratory Manual, Cold Spring Harbor Laboratory (1991).

The present invention will now be described in more detail with reference to the following specific, non-limiting examples.

EXAMPLES

Example 1
Identification and Cloning of B. thuringiensis spoVBt1 gene:

A. Preparation of transposon Tn917 bearing plasmid PLTV1.

Plasmid pLTV1 is isolated from the B. subtilis strain PY1177. The strain is grown overnight (18–20 hours) on TBAB plates (3.3% Difco Tryptose Blood Agar Base) containing 0.5% glucose and $Tet^{10}$ (10 µg/ml). Cells from single colonies are used to inoculate 10 ml LB (1% Bacto Tryptone, 0.5% Bacto Yeast Extract, 0.5% NaCl, pH 7.0) containing 0.5% glucose and $Tet^{10}$ (10 µg/ml). The cells are incubated for 5 hours with shaking (300 rpm) at 37° C., centrifuged at 18,500×g and 4° C. for 10 minutes, then washed once in 10 ml of SET buffer [20% sucrose, 50 mM disodium ethylenediaminetetra-acetic acid (EDTA), 50 mM Tris-HCl pH 8.0]. The pellet is resuspended in 500 µl SET solution containing 2 mg/ml of lysozyme and 0.4 mg/ml RNase A (Boehringer Mannheim Biochemicals, Indianapolis, Ind.). The cell suspension is incubated at 37° C. for 10 minutes and 1 ml of the lysis mixture [1% sodium dodecycl sulfate (SDS), 200 mM NaOH] is added, followed by 725 µl of prechilled neutralization buffer (1.5M potassium acetate pH 4.8). The mixture is then incubated on ice for 20 minutes; centrifuged at 18,500×g and 4° C. for 10 minutes; and the supernatant is transferred to a fresh tube. Plasmid DNA is then isolated using a Mini Qiagen Plasmid Kit (Qiagen Inc., Chatsworth, Calif.).

B. Transfer of pLTV1 to E. coli GM2163.

Unless otherwise indicated, E. coli and B. thuringiensis strains are grown at 37° C. and 30° C., respectively.

Plasmid pLTV1 requires conditioning in a dcm(–) host cell prior to transformation of B. thuringiensis. This is accomplished by transfer of pLTV1 into dcm(–) E. coli GM2163 (New England Biolabs, Inc., Beverly, Mass.). Competent E. coli GM2163 cells are prepared by inoculating a single colony into 30 ml SOB medium (2% Bacto Tryptone, 0.5% Bacto Yeast Extract, 0.06% NaCl, 0.05% KCl, 10 mM $MgCl_2$, 10 mM $MgSO_4$). The cells are incubated overnight at 300 rpm and 37° C. Two hundred ml of SOB media, in a 2 L flask, is inoculated with 8 ml of the overnight culture, and incubated at 37° C. and 300 rpm to an $OD_{550}$ of 0.3. The culture is placed on ice for 15 min., centrifuged at 4,000×g and 4° C. for 5 minutes, and the pellet gently resuspended in 64 ml of transformation buffer 1 (1.2% RbCl, 0.99% $MnCl_2.4H_2O$, 30 mM potassium acetate pH 5.8, 0.25% $CaCl_2.2H_2O$, 15% glycerol). After a 15 minute incubation on ice, the cells are again centrifuged at 4,000×g and finally resuspended in 16 ml of transformation buffer 2 (10 mM MOPS pH 7.0, 0.12% RbCl, 1.1% $CaCl_2.2H_2O$, 15% glycerol). Approximately 50 µl of competent cells and 4 µl DNA are mixed in a 1.5 ml Eppendorf tube and incubated on ice for 1 minute. The mixture of cells and DNA (pLTV1 isolated from B. subtilis strain PY1177) are transferred to a prechilled 0.2 cm gap electrode cuvette and pulsed using the high voltage Gene Pulser electroporation apparatus. The electroporation conditions were 25 µF, 2.5 kV, and 200 Ω. Cells are immediately transferred to 1 ml SOC medium (2% Bacto Tryptone, 0.5% Bacto Yeast Extract, 0.06% NaCl, 0.05% KCl, 20 mM glucose) and incubated at 37° C. and 225 rpm for 1 hr. The cells are plated on LB agar containing $Amp^{75}$ (75 µg/ml) and incubated overnight at 37° C. Plasmid pLTV1 is isolated from transformed E. coli GM2163 cells using the Mini Qiagen Plasmid Kit.

C. Transfer of pLTV1 to B. thuringiensis Cry-B.

The B. thuringiensis strain HD1Mit9 was used for transposon mutagenesis. This strain was obtained from Dr. Arthur I. Aronson at Purdue University. It is an acrystalliferous derivative of B. thuringiensis subspecies kurstaki HD1 and contains only one 4-mDa plasmid.

Plasmid pLTV1 isolated from E. coli is unstable in HD1Mit9. As a result, the plasmid DNA from GM2163 is transformed into Cry⁻B, a plasmid cured crystal-minus strain of B. thuringiensis (Stahly, D. P., Dingmann, D. W., Bulla, L. A. and Aronson, A. I., Biochem. Biophys. Res. Com. 84:581–588, 1978). To prepare competent cells, Cry⁻B is grown overnight on an LB plate. Individual colonies are used to inoculate 100 ml of BHIS medium (3.7% Brain Heart Infusion, 0.5M sucrose) in a 1 L flask. The culture is incubated at 37° C. with shaking, until an $OD_{600}$ of 0.2–0.3. The cells are transferred to a prechilled 250 ml bottle and centrifuged for 7 minutes, at 6,500×g and 4° C. The pellet is washed once in 100 ml and twice in 10 ml of ice cold HEPES (N-[2-hydroxyethyl]piperazine-N'-[2-ethanesulfonic acid])/sucrose wash solution (5 mM HEPES, pH 7.0, 0.5M sucrose). Cells are then resuspended in a solution containing 10 ml of HEPES/sucrose solution and 2.5 ml of 50% glycerol. Competent B. thuringiensis cells (200 µl) are mixed with 10 µl of plasmid DNA pLTV1 (1–5 µg) in a prechilled 0.2 cm gap electrode Gene Pulser Cuvette, and exposed to an electrical current in the Gene Pulser electroporation apparatus (Bio-Rad Laboratories, Richmond, Calif.). The parameters for the electroporation of Cry⁻B are 1.05 kV, 25 µF, Ω=∞. Following electroporation the cells are immediately transferred to 5 ml BHIS in a 125 ml flask and grown at 30° C. and 250 rpm. After three hours of growth, the cells are transferred to LB agar plates containing $Tet^{10}$. The plates are incubated overnight at 30° C. and the transformants, designated Cry⁻B(pLTV1) are restreaked onto fresh LB $Tet^{10}$ plates.

D. Isolation of Plasmid pLTV1 from B. thuringiensis Strain Cry-B.

Cry⁻B(pLTV1) is streaked onto LB $Tet^{10}$ plates. The culture is grown overnight. A single colony is restreaked onto an SA plate (1× Spizizens salts, 1% casamino acids, 0.5% glucose, 0.005 mM $MnSO_4.H_2O$, 1.5% Bacto agar) and incubated for 3–4 hours at 37° C. The 1× Spizizens salts contain 0.2% $(NH_4)_2SO_4$, 1.4% $K_2HPO_4$, 0.6% $KH_2PO_4$, 0.1% Sodium-Citrate $2H_2O$, and 0.02% $MgSO_4.7H_2O$ (Anagnostopoulos and Spizizen, 1961). The grown cells are removed from the plate, resuspended in 100 μl TESL (100 mM Tris-HCl pH 8.0, 10 mM EDTA, 20% sucrose, 2 mg/ml lysozyme) and incubated at 37° C. for 30–60 minutes. Two hundred microliters of lysis solution (200 mM NaOH, 1% SDS) is added to the tube followed by a 5 minute incubation at room temperature. After addition of 150 μl ice-cold 3M potassium acetate pH 4.8, the suspension is microcentrifuged for 20 minutes at 18,500×g and 4° C. The supernatant is transferred to a fresh tube and mixed with 1 ml of 100% ethanol. This suspension is left at −20° C. for 1 hour and centrifuged at 18,500×g and 4° C. for 30 minutes. The plasmid DNA is washed with 70% ethanol, dried under vacuum, and resuspended in 20 μl of TE.

E. Transfer of pLTV1 to B. thuringiensis Strain HD1Mit9.

Plasmid pLTV1 isolated from $Cry^-B$(pLTV1) is introduced into strain HD1Mit9. *B. thuringiensis* HD1Mit9 cells (Dr. Arthur I. Aronson, Purdue University) are made competent and transformed using the same procedure described above for $Cry^-B$. The plasmid is isolated from HD1Mit9 (pLTV1) using the same protocol used for $Cry^-B$(pLTV1). However, the parameters for the electroporation of HD1Mit9 are 1.2 kV, 3 μF, Ω=∞. The presence of plasmid pLTV1 in the HD1Mit9 transformants was confirmed by restriction enzyme digestion and polymerase chain reaction (PCR). The results of each experiment are analyzed by agarose gel electrophoresis. The pLTV1 DNA (1 μg), isolated from HD1Mit9, is digested with EcoRI (Pharmacia Biotechnology, Piscataway, N.J.) under the conditions described by the manufacturer. Primers LacNHS1, SEQ ID NO.3 and LacNHS2, SEQ ID NO.4, used for the PCR reactions, are synthesized on a PCR-Mate DNA synthesizer model 391 (Applied Biosystems, Foster City, Calif.).

| Primer | Sequence (5'-3') | SEQ ID NO. |
|---|---|---|
| LacNHS1 | GGCTTTCGCTACCTGGAGAGACGCGCCCGC | 3 |
| LacNHS2 | CCAGACCAACTGGTAATGGTAGCGACCGGC | 4 |

A single *B. thuringiensis* colony is resuspended in 15 μl sterile water, placed in a boiling water bath for 10 minutes, and then centrifuged for 5 minutes. Each PCR reaction contained 2 μl of the supernatant from the boiled cells, 1× PCR buffer [100 mM Tris-HCl pH 8.3, 500 mM KCl, 15 mM $MgCl_2$, 0.1% (wt/vol) gelatin], 200 μM deoxyribonucleoside triphosphates (dNTP's; 1.25 mM of dATP, dCTP, dGTP, and dTTP), 1 μM LacNHS1 primer, 1 μM LacNHS2 primer, and 2.5 units AmpliTaq DNA polymerase (Perkin-Elmer Cetus, Norwalk, Conn.). The reactions are run in a DNA Thermal Cycler (Perkin-Elmer Cetus) for 25 cycles. Each cycle consists of 1 minute at 94° C. (denaturation), 2 minutes at 55° C. (hybridization), and 3 minutes at 72° C. (extension). The PCR products are analyzed by agarose gel electrophoresis. Synthesis of a 1.5 kb PCR generated fragment indicates that the clone carried the pLTV1 plasmid.

F. Preparation of Tn917 Insertion Libraries.

To prepare the library, HD1Mit9 (pLTV1) is grown on an LB plate containing $Tet^{10}$. Two to three colonies are used to inoculate 10 ml Penassay broth (1.75% Difco Antibiotic Medium 3) containing $Ery^{0.15}$. After 90 minutes of growth at 30° C. and 300 rpm, the concentrations of antibiotics in the culture are increased to $Ery^1$ and $Lm^{25}$. When the culture reaches an $OD_{595}$ of 0.5, a 100 μl portion is added to 10 ml fresh Penassay broth containing $Ery^1$ and $Lm^{25}$. After 16 hours of growth at 39° C. and 300 rpm, the culture is diluted 1:15 with 10 ml Penassay broth containing $Ery^1$ and $Lm^{25}$ and grown with moderate shaking at 39° C. until an $OD_{595}$ of 2.0. The cells are pelleted by centrifugation (4,000×g, 4° C.), resuspended in 500 μl of Penassay broth containing $Ery^1$ and 30% glycerol, and frozen on dry ice. Dilutions ($10^{-3}$ and $10^{-4}$) of the library are plated onto Penassay $Ery^5$ plates and incubated at 39° C. for 16 hours. Individual colonies are patched onto LB plates each containing different antibiotics ($Tet^{10}$, $Lm^{25}$, and $Ery^5$) and grown overnight at 30° C. Those colonies that grow only on LB Lm25 and LB $Ery^5$ but not LB $Tet^{10}$ contained Tn917 insertions. These colonies are grown on CYS plates (1% Casitone, 0.5% glucose, 0.2% Bacto Yeast Extract, 0.1% $KH_2PO_4$, 0.5 mM $MgCl_2$, 0.05 mM $MnCl_2$, 0.05 mM $ZnSO_4$, 0.05 mM $FeCl_2$, 0.2 mM $CaCl_2$, 1.5% Bacto agar and examined microscopically for their ability to sporulate. Over $1\times10^4$ colonies are screened for transposon insertions. Sixty-three colonies containing a chromosomal insertion are obtained. Only three colonies (5% of the insertion mutants) are sporulation-defective. The sporulation mutants are further analyzed.

To identify auxotrophs and citric acid cycle-defective colonies, the *B. thuringiensis* sporulation mutants are grown on glucose minimal and lactate minimal plates for 1–2 days, and the growth is compared to that of HD1Mit9. Glucose minimal agar is made of 1× salt solution [1 liter; 5.6 g $K_2HPO_4$, 2.4 g $KH_2PO_4$, 1.2 g $(NH_4)_2SO_4$, 0.4 g sodium citrate, pH 7.0], 0.005 mM $FeCl_2$, 0.25 mM $MgCl_2$, 0.96% glucose, 0.0002 mM $MnCl_2$, 0.00012% Thiamine-B1, and 1.5% Bacto agar. Lactate minimal medium contains 0.2% lactate and 25 mM glutamate instead of glucose and sodium citrate. The three sporulation mutants grow well on glucose and lactate minimal media indicating that they are not auxotrophs or defective in citric acid cycle enzymes.

G. Isolation of DNA from the *B. thuringiensis* Sporulation Mutant.

The sporulation mutant strain, HD1Mit9::Tn917, is grown in 2 ml LB overnight at 200 rpm. The overnight culture is used to inoculate 100 ml LB (1% inoculation). The cells are grown at 300 rpm to an $OD_{600}$ of 0.7–1.0, collected by centrifugation (3,840×g, 5 minutes, 4° C.), and resuspended in 5 ml TES (25 mM Tris-HCl pH 8.0, 25 mM EDTA, 25% sucrose). The cell suspension is mixed with 0.55 ml of 10 mg/ml lysozyme in TES solution and incubated at 37° C. for 60 minutes. SDS is added to 2% weight-to-volume, followed by a 15 minute incubation at 50° C. The suspension is mixed with 1.52 ml of 5M NaCl and incubated at 50° C. for 5 minutes. The sample is incubated at 0° C. for 1 hour, centrifuged for 10 minutes at 18,500×g and 4° C., and the supematant is transferred to a new tube. To purify the DNA from the protein, the supematant is treated with phenol and chloroform. First, it is mixed with 5 ml TE-equilibrated phenol followed by 15 minutes incubation at 50° C., then with 5 ml phenol/chloroform (1:1), and finally with 5 ml chloroform. The aqueous phase is separated from the organic phase by centrifugation (4,000×g, 5 minutes) at each step. The DNA is precipitated by the addition of 4.6 ml isopropanol and centrifugation (18,500×g, 30 minutes, 4° C.). The air-dried DNA pellet was dissolved in 2 ml of TE and stored at −20° C.

H. Cloning the Chromosomal DNA Adjacent to Transposon Insertions.

*B. thuringiensis* chromosomal DNA is cloned and maintained in *E. coli* DH5α (Gibco BRL, Grand Island, N.Y.) or HB101 (New England Biolabs, Inc.) strains. Restriction enzymes, T4 DNA Ligase, and reaction buffers are purchased from New England Biolabs, Inc., Pharmacia Biotechnology (Piscataway, N.J.), or Gibco BRL. Competent *E. coli* cells were prepared as follows. The strains are incubated on LB agar plates for 16–18 hours. Several colonies are used to inoculate 100 ml LB in 1L Erlenmeyer flasks. Liquid cultures are grown at 37° C. and 300 rpm. When the cultures reach an $OD_{600}$ of 0.2, they are placed on ice for 15 minutes and then centrifuged for 10 minutes at 5,500×g and 4° C. The cells are resuspended in 50 ml (½ volume) 0.05M $CaCl_2$, incubated on ice for 20 minutes, and centrifuged as described above. The competent cells are resuspended in 5 ml (1/20 volume) 50 mM $CaCl_2$ containing 20% glycerol and placed into microfuge tubes (100 μl per tube).

*B. thuringiensis* chromosomal DNA (11–14 μg) is digested with a restriction enzyme as follows. Reactions contain 30–50 units of enzyme in a 1× reaction buffer and are incubated overnight at 37° C. The 10× reaction buffers include REact 2 (500 mM Tris-HCl pH 8.0, 100 mM $MgCl_2$, 500 mM NaCl), REact 3 (500 mM Tris-HCl pH 8.0, 100 mM $MgCl_2$, 1M NaCl), and NEB 3 [500 mM Tris-HCl pH 8.0, 100 mM $MgCl_2$, 10 mM dithiothreitol (DTT), 1M NaCl]. The REact 2, REact 3, and NEB 3 buffers are used for the XbaI, EcoRI, and BspEI enzymes, respectively. The enzymes are inactivated by heating at 70° C. for 40 minutes. Digested DNA is ligated in a 100 μl volume using 16 units of T4 DNA Ligase and 20 μl of 5× Ligase Reaction Buffer [50 mM $MgCl_2$, 25% (wt/vol) polyethylene glycol 8000, 5 mM ATP, 5 mM DTT, 250 mM Tris-HCl pH 7.6] and incubated overnight at 16° C. The ligated mixtures are used to transform 100 μl *E. coli* HB101 competent cells. Ampicillin-resistant transformed colonies are isolated after 16 hours of growth on LB agar containing $Amp^{75}$. Plasmid DNA is extracted from the HB101 transformants, transferred to *E. coli* DH5α or GM2163, and then analyzed by restriction endonuclease digestion.

I. Determination of the Nucleotide Sequence of spoVBt1.

Both strands of the cloned gene are sequenced using the primers listed in Table 1 which are synthesized on a PCR-Mate DNA synthesizer model 391. The positions of the oligonucleotides are shown in FIG. 2. A Sequenase Version 2.0 DNA Sequencing Kit (United States Biochemical, Cleveland, Ohio) is used to sequence the cloned *B. thuringiensis* chromosomal fragments as described by the manufacturer. The sequence of spoVBt1 gene is shown in SEQ ID NO.1. The molecular mass of the spoVBt1 gene product is 36.7 kDa.

TABLE 2

Primers used for sequencing *B. thuringiensis* spoVBtl gene

| Primer | Sequence (5'-3') | SEQ ID NO. |
|---|---|---|
| MS1 | GAGAGATGTCACCGTCAAG | 5 |
| MS2 | CCCTGTACCTGGATTCCC | 6 |
| MS3 | GGGAATCCAGGTACAGGG | 7 |
| MS4 | CCATCCCAACAAGCTTCCC | 8 |
| MS5 | GGGAAGCTTGTTGGGATGG | 9 |
| MS6 | CCTGTCCCCCTTGTAAATGC | 10 |

TABLE 2-continued

Primers used for sequencing *B. thuringiensis* spoVBtl gene

| Primer | Sequence (5'-3') | SEQ ID NO. |
|---|---|---|
| MS7 | GCATTTACAAGGGGGACAGG | 11 |
| MS8 | CGCCGTCTACTTACAAGCAGC | 12 |
| MS9 | GGTGGTGGGACTATGGAG | 13 |
| MS10 | CTCCATAGTCCCACCACC | 14 |
| MS11A | CGAGGAGGAGAGAAGGAC | 15 |
| MS11B | GTCCTTCTCTCCTCCTC | 16 |
| MS12A | CGAAGTGTACGGTCTGG | 17 |
| MS12B | CACGATGCATCG | 18 |
| MS13A | CGAAAGAGGCTGAATGG | 19 |
| MS13B | GGGCGGTATGTACGG | 20 |
| MS13C | CCGTACATACCGCCC | 21 |
| MS14 | GCATCAAATCCATACTCGATATTCC | 22 |
| MS14A | CGAGTATGGATTTGATGCTCG | 23 |
| MS16 | GGACACGATCCTAATTCAGC | 24 |
| MS16A | GCTGAATTAGGATCGTGTCC | 25 |

J. Characterization of Spores from the sporulation mutant strain HD1Mit9:: Tn917.

The resistance properties of the mutant and the wild type spores of HD1Mit9 against heat, lysozyme, and organic solvents are compared. The wild type and mutant strains are grown in 100 ml CYS medium. The cultures are harvested 48 hours after they reached stationary phase. The sporulated cultures are then exposed to various treatments, and serial dilutions in 0.1% peptone are plated onto LB agar and incubated overnight at 30° C. Colonies arising from germinated spores are counted. Resistance of spores to heat, lysozyme, and organic solvents is determined. Heat Treatment: Cultures are diluted 1:10 in 0.1% sterile peptone and divided into two equal parts. One part is incubated at 55° C. and the other at 65° C. for 45 minutes with occasional mixing. Lysozyme Treatment: Cultures are diluted 1:100 in 0.1% peptone containing 250 μg/ml lysozyme and incubated at 37° C. for 15 minutes. Organic Solvent Treatment: Samples are treated with toluene, 1-octanol, and chloroform using the following protocol. One milliliter of the cultures is mixed with 7 ml of 0.1% peptone and 2 ml of organic solvent. The mixtures are then vortexed for 1 minute. For the acetone treatment, the cultures are diluted 1:10 in acetone and incubated at room temperature for 15 minutes. The mutants spores are sensitive to heat and organic solvents and resistant to lysozyme. The relative resistance of spores produced by the sporulation mutant strain, from the most resistant to the least resistant, are as follows: lysozyme, heat, toluene, chloroform, acetone, and 1-octanol.

Example 2

Chromosomal Integration

A. Preparation of the spoVBt1 DNA sequence and a mutated spoV DNA sequence.

The spoVBt1 DNA sequence is prepared as described above in Example 1. Primers MS18, MS19A, MS19B and MS20 are used to PCR amplify a mutated spoV gene using the native spoVBt1 as a template. The primers are designed to contain several point mutations such that the putative ribosomal binding site and the start codon are destroyed and multiple stop codons are introduced throughout the spoVBt1 sequence. This mutated spoV DNA sequence corresponds to nucleotide sequence 465 to 1256 of SEQ ID No.1 with alterations as indicated in Table 1. The specific mutated spoV DNA sequence is designated (m) spoVBt1-8.

| Primer | Sequence (5'-3') | SEQ ID NO. |
|---|---|---|
| MS18 | GATGTGATTGTAAGGAACAATCGAAGCGATAGAAAAAC | 26 |
| MS19A | GATCTTGTATGAGAGTAAATCGGCCATACAGC | 27 |
| MS19B | GCTGTATGGCCGATTTACTCTCATACAAGCTC | 28 |
| MS20 | CTATACAGCATGTTAATGATCCC | 29 |

To obtain the (m)spoVBt1-8 gene, two PCR reactions are involved. The two fragments of the gene, the 3' and the 5' halves of the sequence, containing a 32 bp overlap corresponding to MS19A and MS19B on each DNA strand are amplified. The 5' half is amplified using primers MS18 and MS19B and the 3' half is amplified using primers MS19A and MS20. The two fragments are mixed, denatured and annealed. The entire (m)spoVBt1-8 gene is amplified using primers MS18 and MS20.

B. Chromosomal Integration of crystal genes at the spoV gene Bt1 site with the (t) spoVBt1-1.

Figure 6:
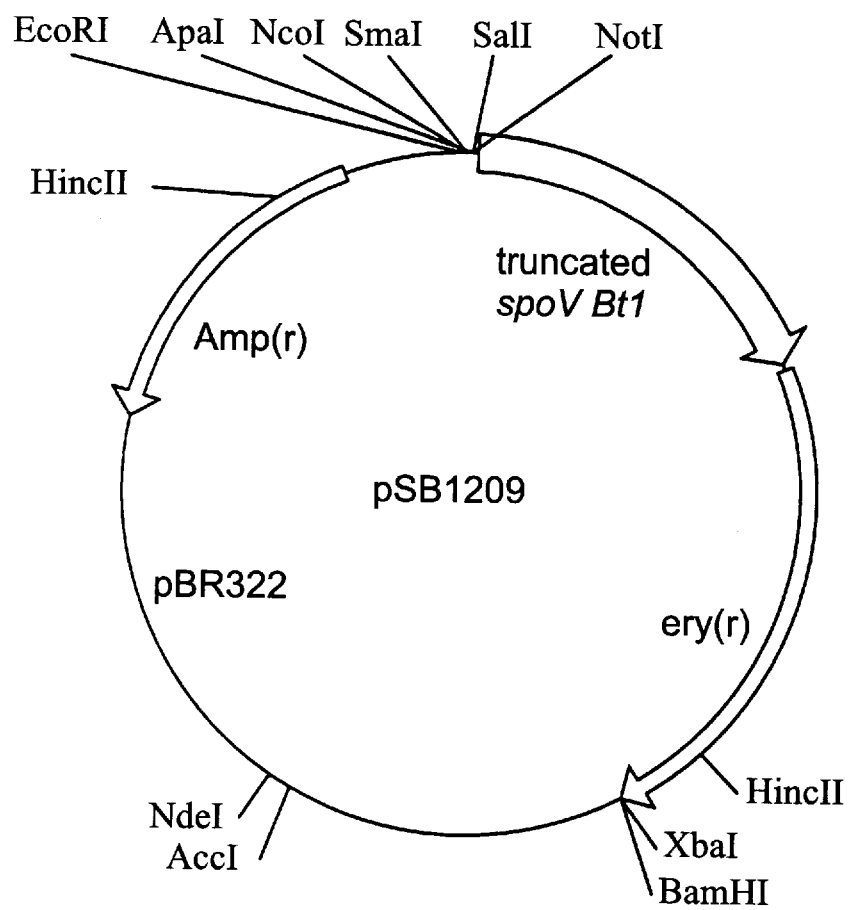
FIG. 6 illustrates plasmid pSB1209.

Crystal genes are integrated into the B. thuringiensis chromosome using the pSB1209 plasmid (FIG. 6).

Figure 3:
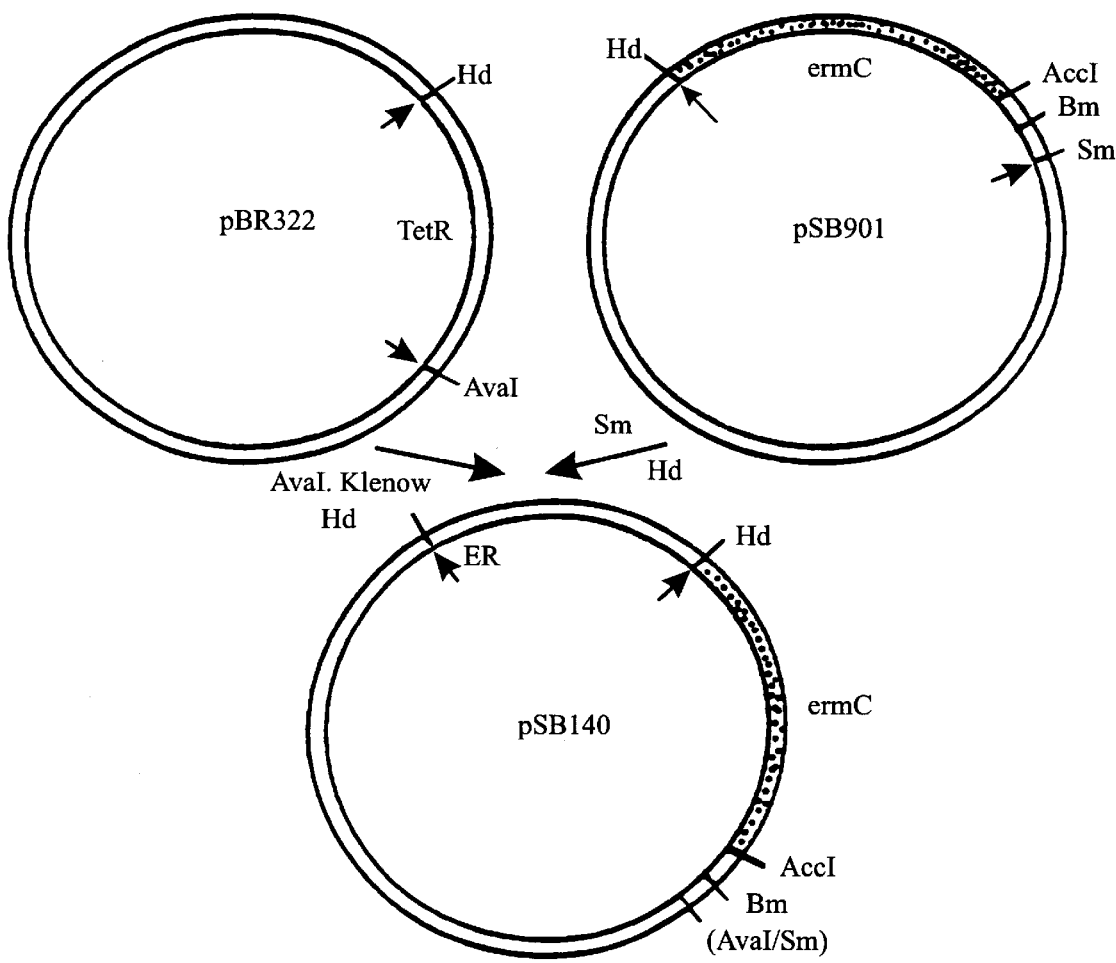
FIG. 3 illustrates the plasmids, pSB901, pBR322 and pSB140.
Figure 4:
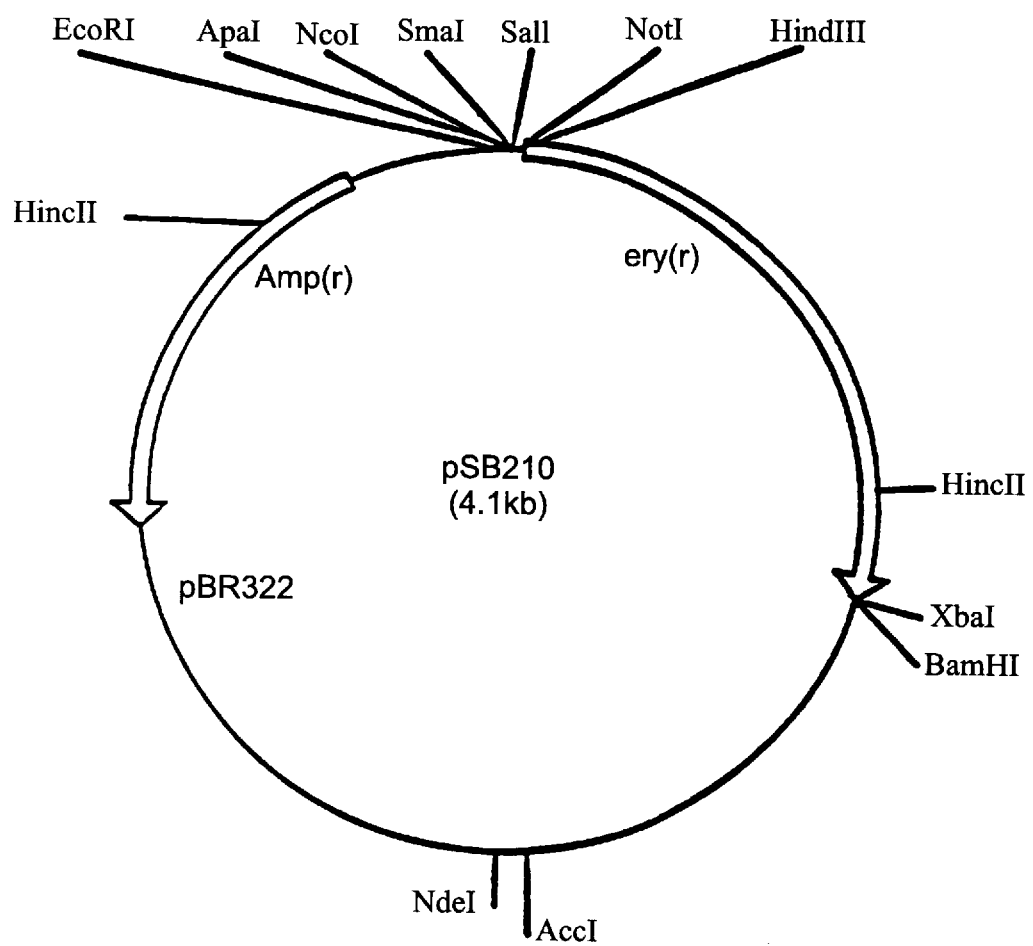
FIG. 4 illustrates plasmid pSB210.

The plasmid pSB901 (FIG. 3) is constructed to provide an erythromycin resistance gene, ermC. The ermC gene is isolated as a HindIII/ClaI fragment from the p1M13 Bacillus subtilis plasmid described by Monod et al. [Monod et al., J. Bacteriol. 167:138–147 (1986)]. The ermC HindIII/ClaI fragment is ligated to pUC18 cut with HindIII and AccI. To replace the tetracycline resistance gene (tet$^r$) in pBR322 (FIG. 3) with the ermC gene from pSB901, pBR322 is digested with AvaI and the linearized vector is treated with the Klenow fragment of E. coli DNA polymerase I to generate a blunt end. Following Klenow treatment, pBR322 is digested with HindIII and the large fragment is purified away from the tet$^r$ gene fragment. Plasmid pSB901 is digested with SmaI followed by HindIII and the fragment carrying the ermC SmaI-HindIII fragment is purified. The ermC gene is ligated into the pBR322 HindIII large fragment to generate pSB140 (FIG. 3).

| Primer | Sequence (5'-3') | SEQ ID NO. |
|---|---|---|
| KK14 | AGCTTGCGGCCGCGTCGACCCCGGGCCATGGGGGCCCG | 30 |
| KK14B | AATTCGGGCCCCCATGGCCCGGGGTCGACGCGGCCGCA | 31 |
| MS17 | GCGAAAGAAAAACAACAATC | 32 |

Figure 5:
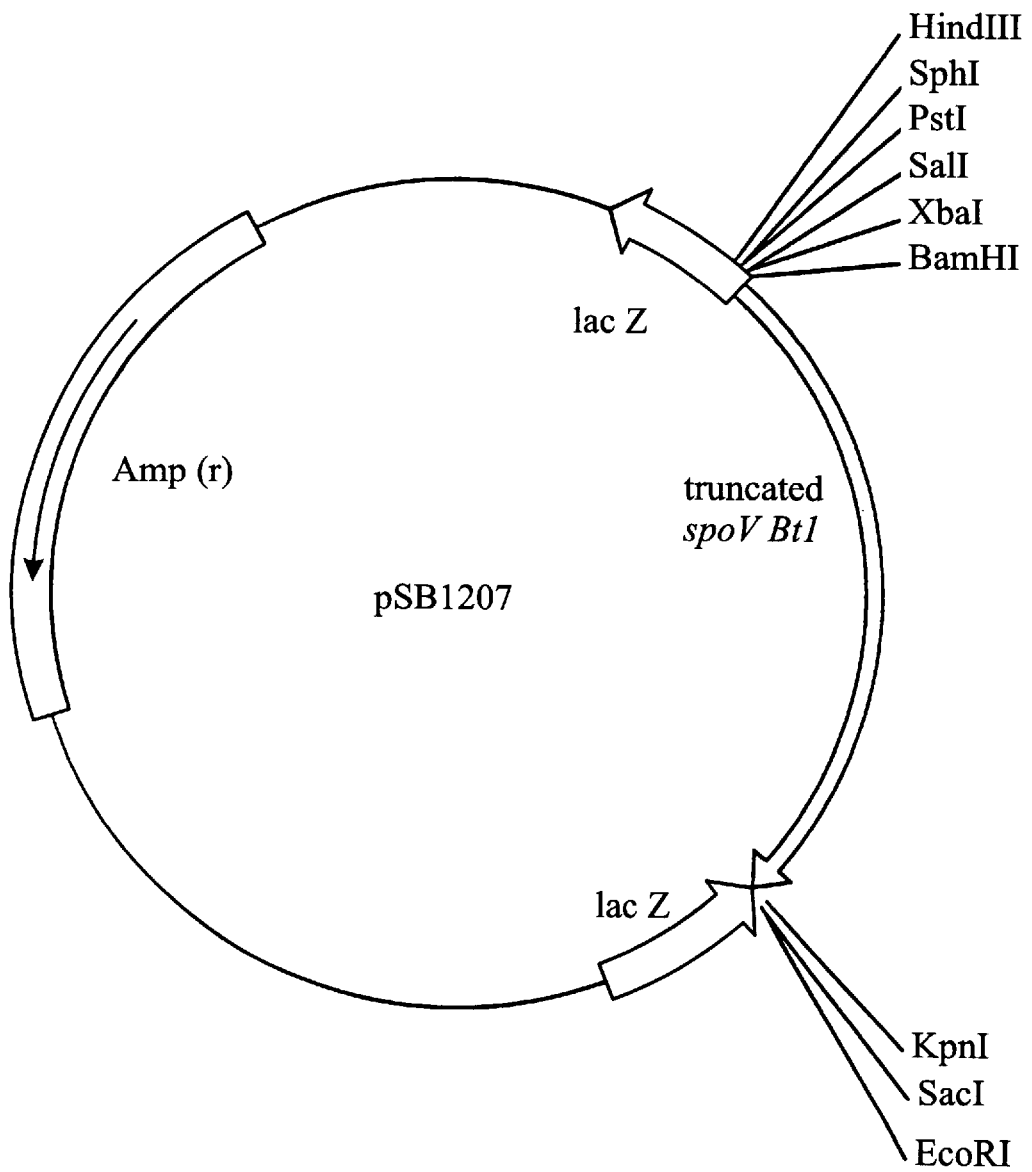
FIG. 5 illustrates plasmid pSB1207.

Using PCR primers, MS14, SEQ ID NO.22, and MS17, SEQ ID NO.32, (t)spoVBt1-1 gene is amplified from B. thuringiensis HD73 strain. The 916 bp PCR product is blunted at both ends using the DNA polymerase I Klenow fragment, and cloned into plasmid pUC18 at the SmaI site. The (t)spoVBt1-1 corresponds to base pair 488 through 1404 of SEQ ID NO.1. The resulting plasmid is called pSB1207 (FIG. 5).

The (t)spoVBt1-1 gene is isolated from pSB1207 using EcoRI and HincII restriction enzymes and the ends were blunted with the Klenow fragment. The pSB210 is linearized using HindIII enzyme, blunted with Klenow, and dephosphorylated using Calf Intestinal alkaline phosphatase (CIP). The isolated (t)spoVBt1-1 gene is then ligated into the linearized pSB210 plasmid. The resulting plasmid is called pSB1209 (FIG. 6). Various crystal genes are cloned at the ApaI and NotI sites of pSB1209 and integrated into the B. thuringiensis chromosome at the spoVBt1 site.

C. Chromosomal Integration of crystal genes at the spoVBt1 site using the (m) spoVBt1-8 fragment.

Figure 7:
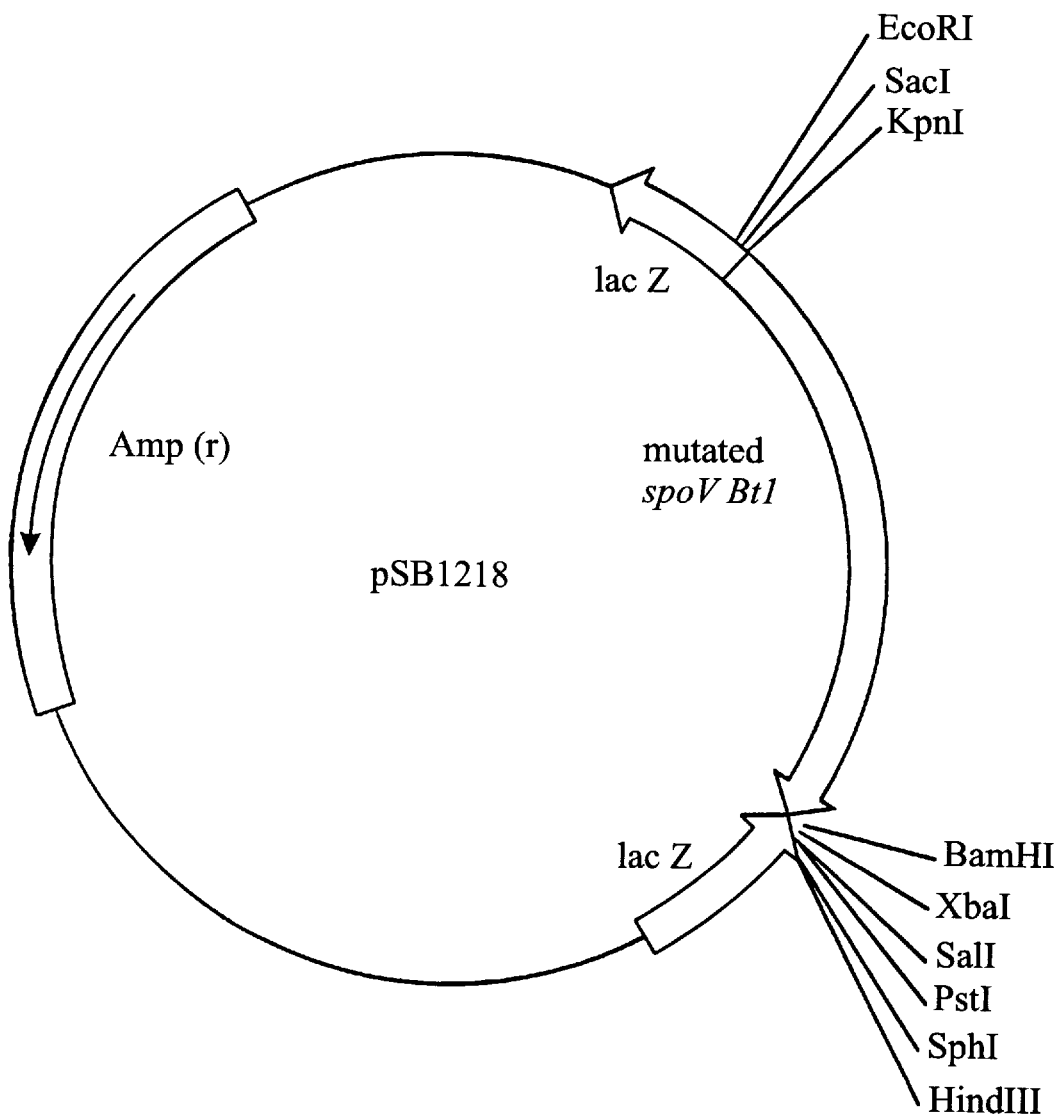
FIG. 7 illustrates plasmid pSB1218.

The (m)spoVBt1-8 fragment is amplified from B. thuringiensis HD73 strain using the PCR technique. The 0.8 kb PCR product is blunted at both ends using the Klenow fragment, and cloned into plasmid pUC19 at the SmaI site. The resulting plasmid is called pSB1218 (FIG. 7).

Figure 8:
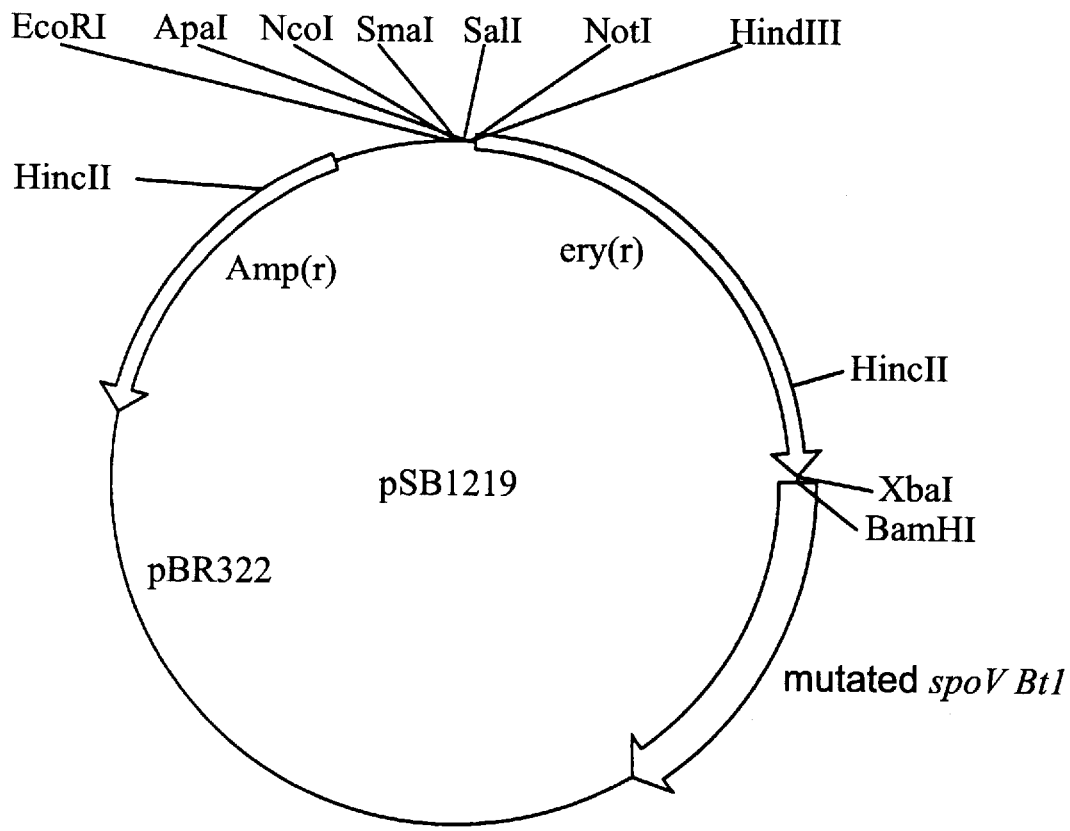
FIG. 8 illustrates plasmid pSB1219.
Figure 9:
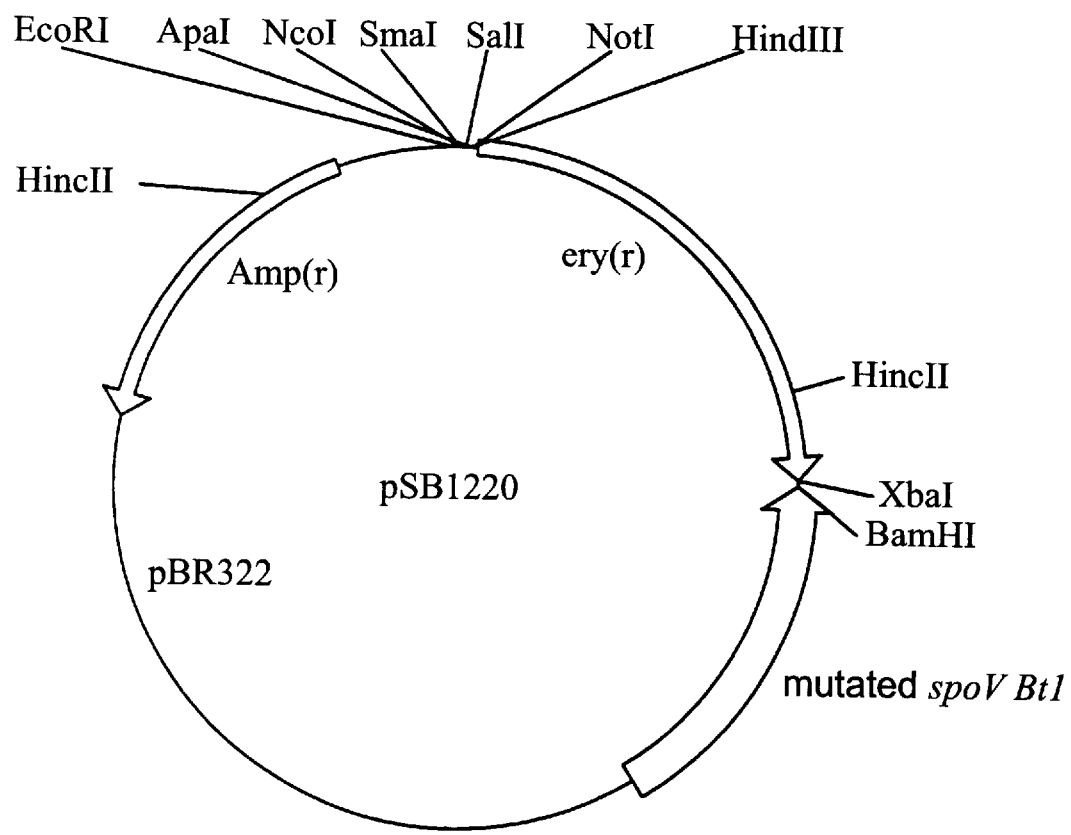
FIG. 9 illustrates plasmid pSB1220.

The (m) spoVBt1-8 fragment is isolated from pSB1218 at the KpnI and BamHI sites. This fragment is blunted at both ends using T4 DNA polymerase, and cloned into plasmid pSB210 at the MscI site. The resulting plasmids are pSB1219 (FIG. 8) and pSB1220 (FIG. 9). The cloned (m) spoVBt1-8 fragment is either in the same orientation as ermC gene in pSB210 (pSB1219) or in the opposite direction of the ermC open reading frame (pSB1220). The G27 gene encoding a CryIC/CryIE hybrid crystal protein is cloned in pSB1219 using the following steps:

To construct the pSB210.1 plasmid, (FIG. 11), the phospholipase C "plc" gene is added to pSB210. The DNA sequence of the plc region from B. thuringiensis strain ATCC 10792 is obtained from Genbank (Accession number X14178) and is described by Lechner et al., [Lechner, M., et al., Mol. Microbiol. 3:621–626 (1989)]. The plc region is amplified from HD73 total DNA by PCR using primers Phos1 and Phos4.

| Primer | Sequence (5'-3') | SEQ ID NO. |
|---|---|---|
| Phos1 | GGAACGCTACATACTAGTGATAGAGTAG | 33 |

-continued

| Primer | Sequence (5'-3') | SEQ ID NO. |
|---|---|---|
| Phos4 | GCTTGTACACCGCAACTGTTTTCGCATG | 34 |

Figure 10:
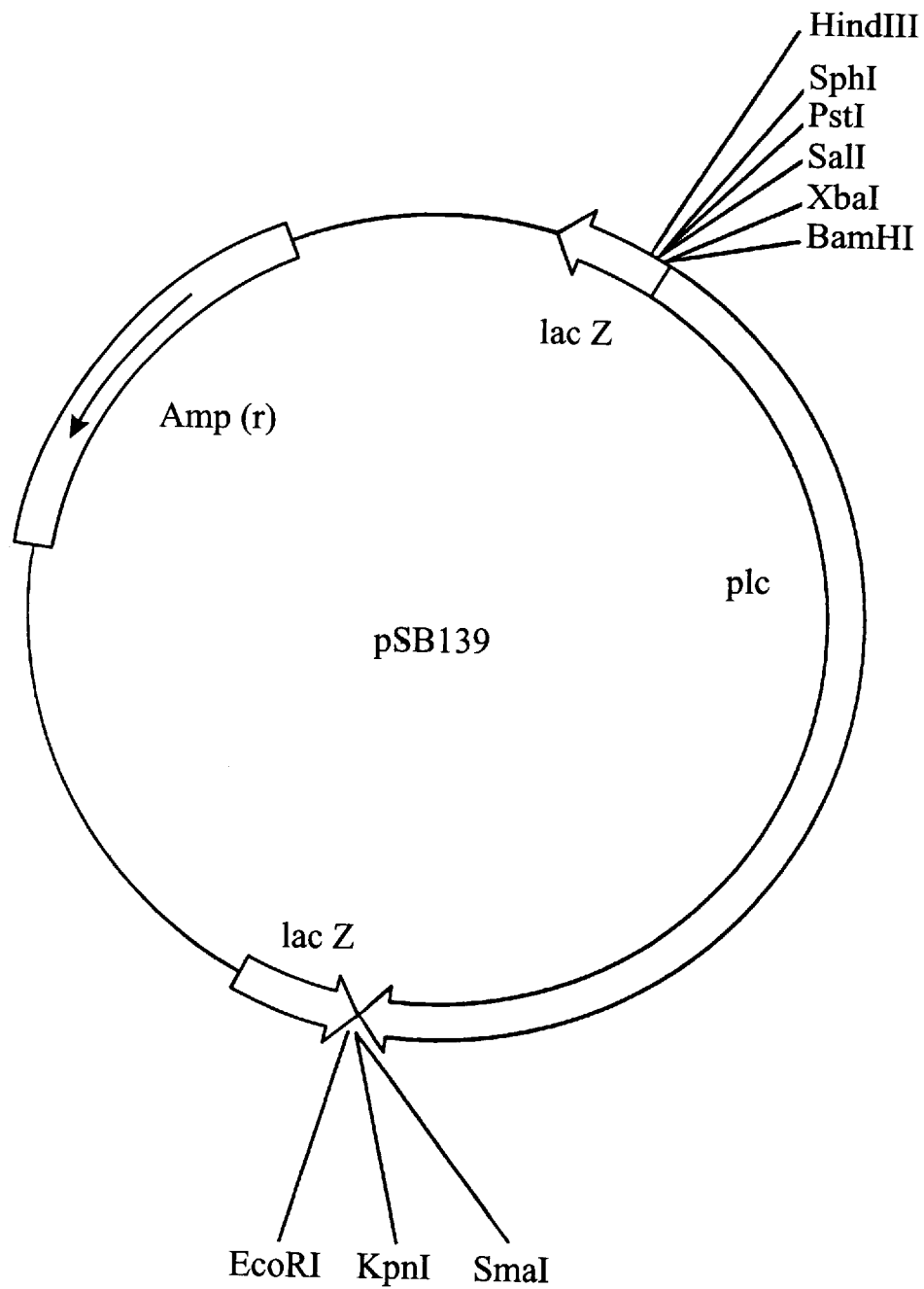
FIG. 10 illustrates plasmid pSB139.
Figure 11:
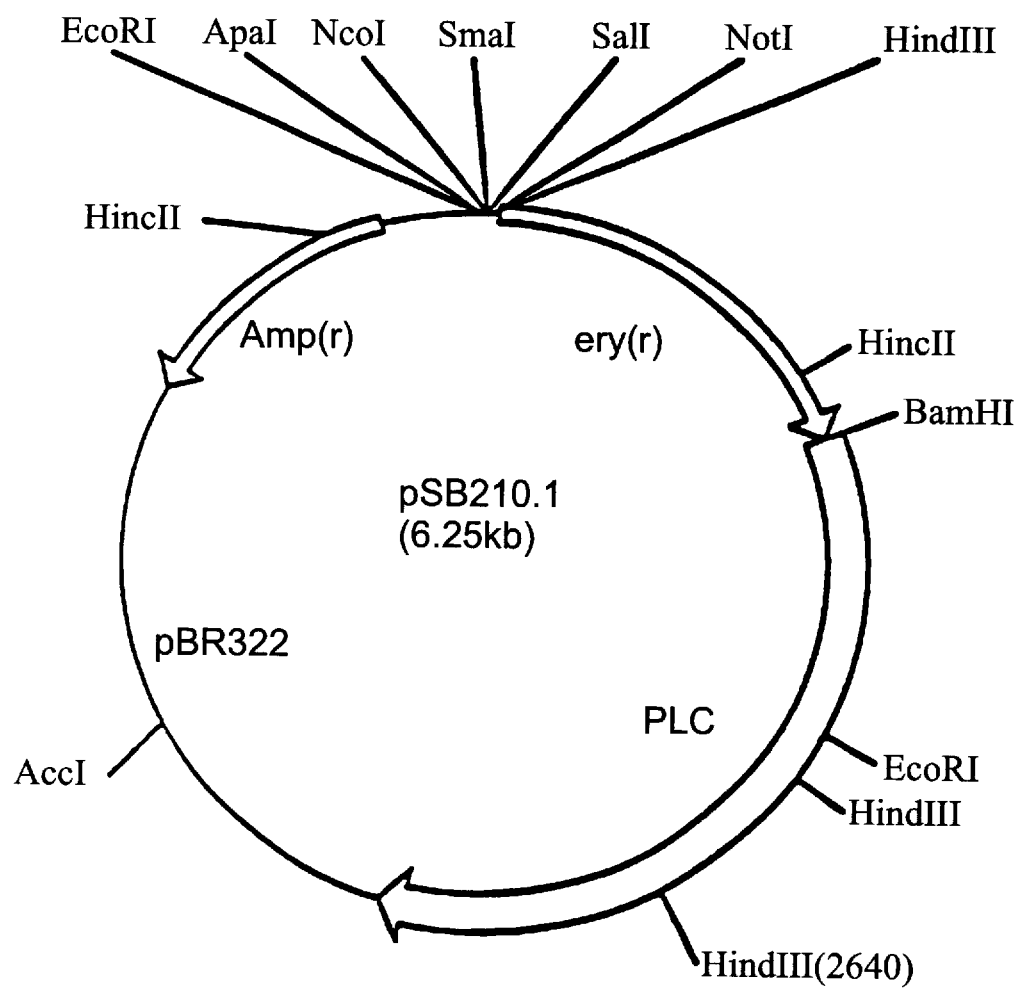
FIG. 11 illustrates plasmid pSB210.1.

The PCR product is cloned into the SmaI site of pUC18 to construct pSB139 (FIG. 10). The plc target region is isolated on a 2.2 kb blunted-KpnI, BamHI fragment from pSB139, gel-purified and ligated into pSB210, which has been digested with MscI and BamHI and purified using the Geneclean Kit (Bio101), following the manufacturer's directions. The resulting plasmid is designated pSB210.1 (FIG. 11).

Figure 12:
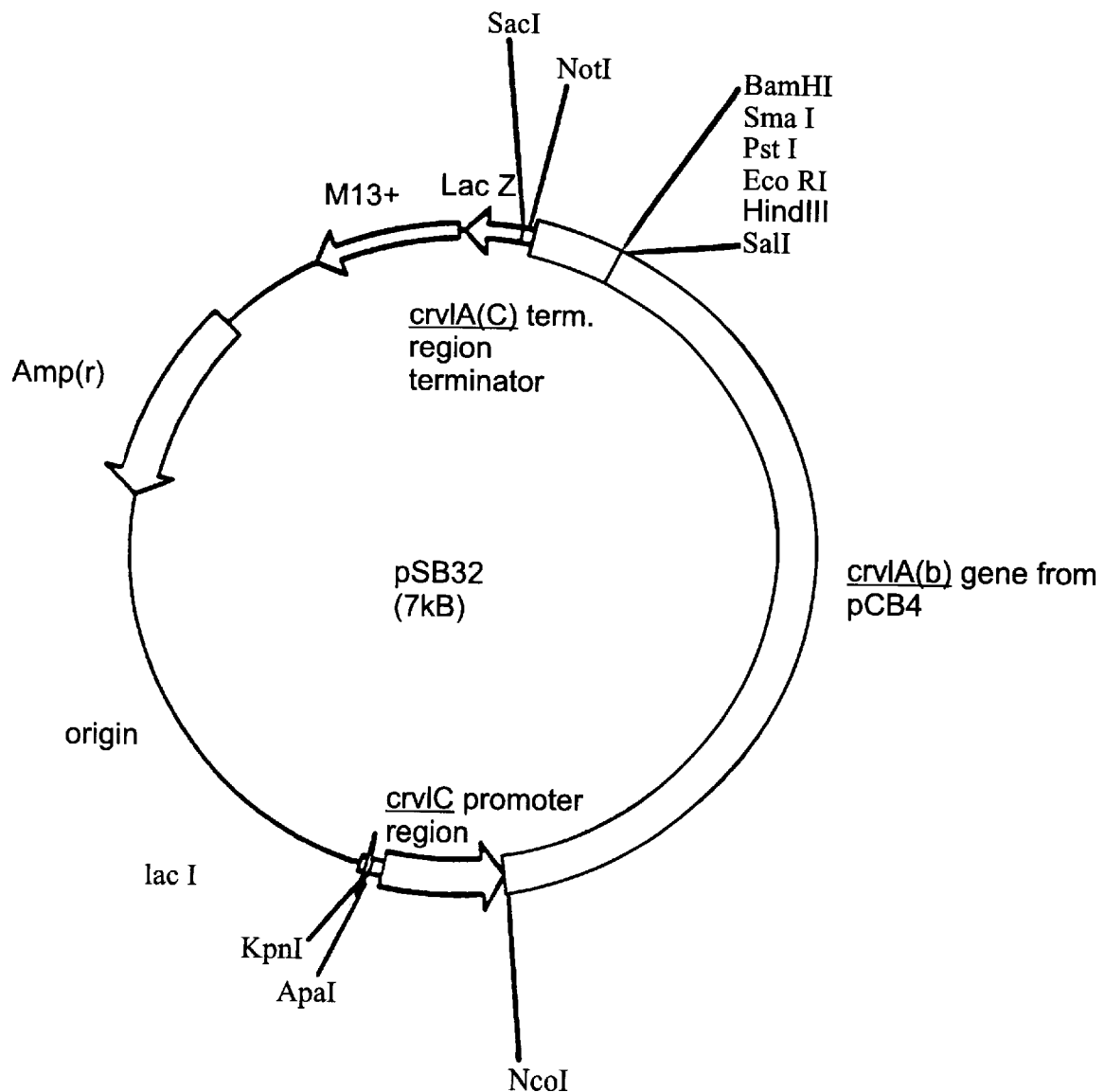
FIG. 12 illustrates plasmid pSB32.
Figure 13:
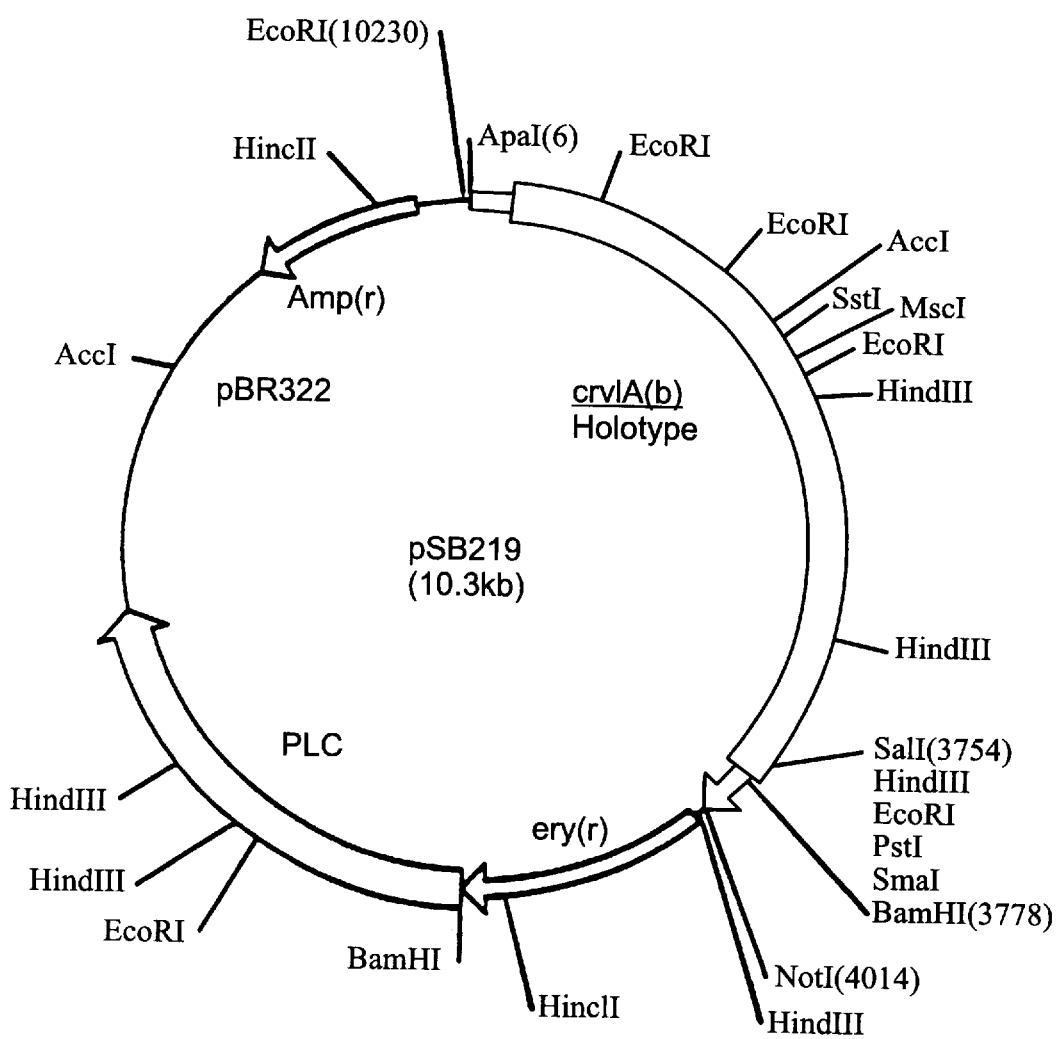
FIG. 13 illustrates plasmid pSB219.

The plasmid pSB32, (FIG. 12) carrying the holotype cryIA(b) gene from B. thuringiensis aizawai, is cut with ApaI and NotI to release the 4.2 kb fragment containing the cryIA(b) gene. This plasmid also contains pBlueScript KS$^+$, cryIC promoter and cryIA(c) terminator which control the expression of cryIA(b) gene. This isolated cryIA(b) fragment is ligated into pSB210.1 cut with ApaI and NotI to generate pSB219 (FIG. 13) containing the cryIA(b), the plc, and the ermC genes.

Figure 14:
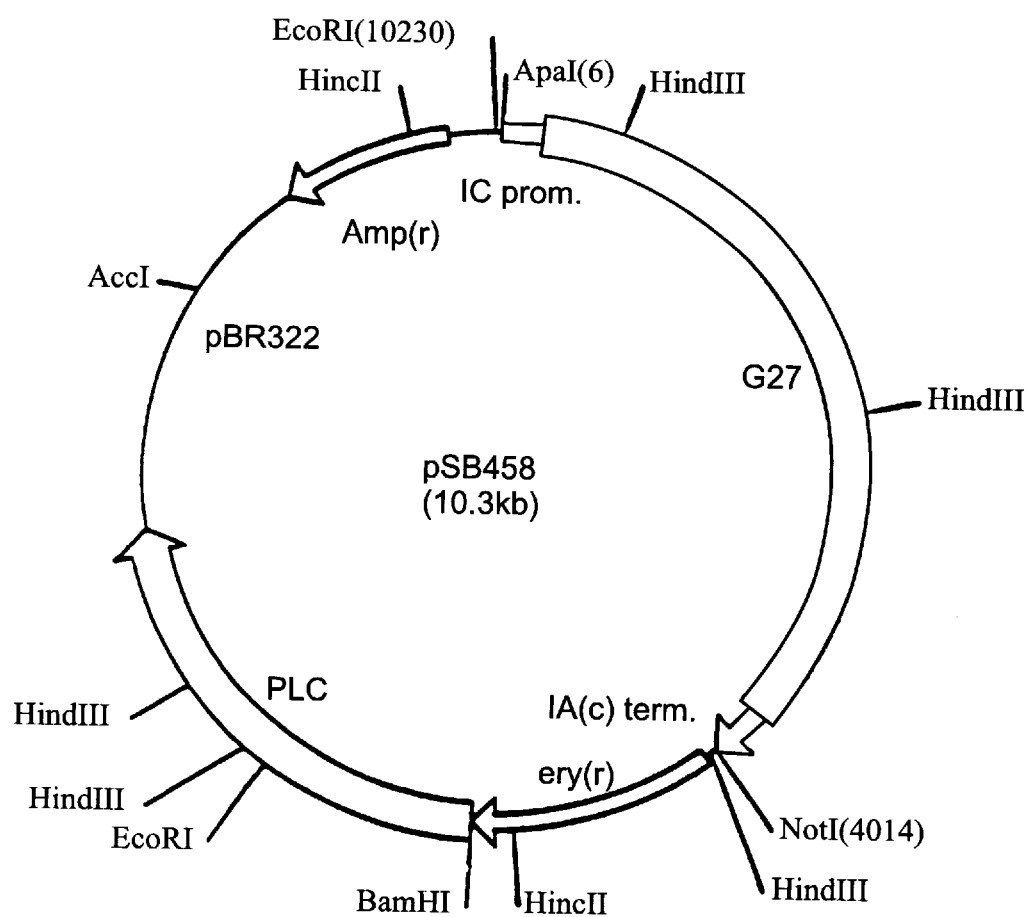
FIG. 14 illustrates plasmid pSB458.

A 3.9 kb ApaI/NotI fragment containing a G27 toxin coding region is ligated to the 6.3 kb ApaI/NotI fragment from pSB219. The resulting plasmid is called pSB458 (FIG. 14).

Figure 15:
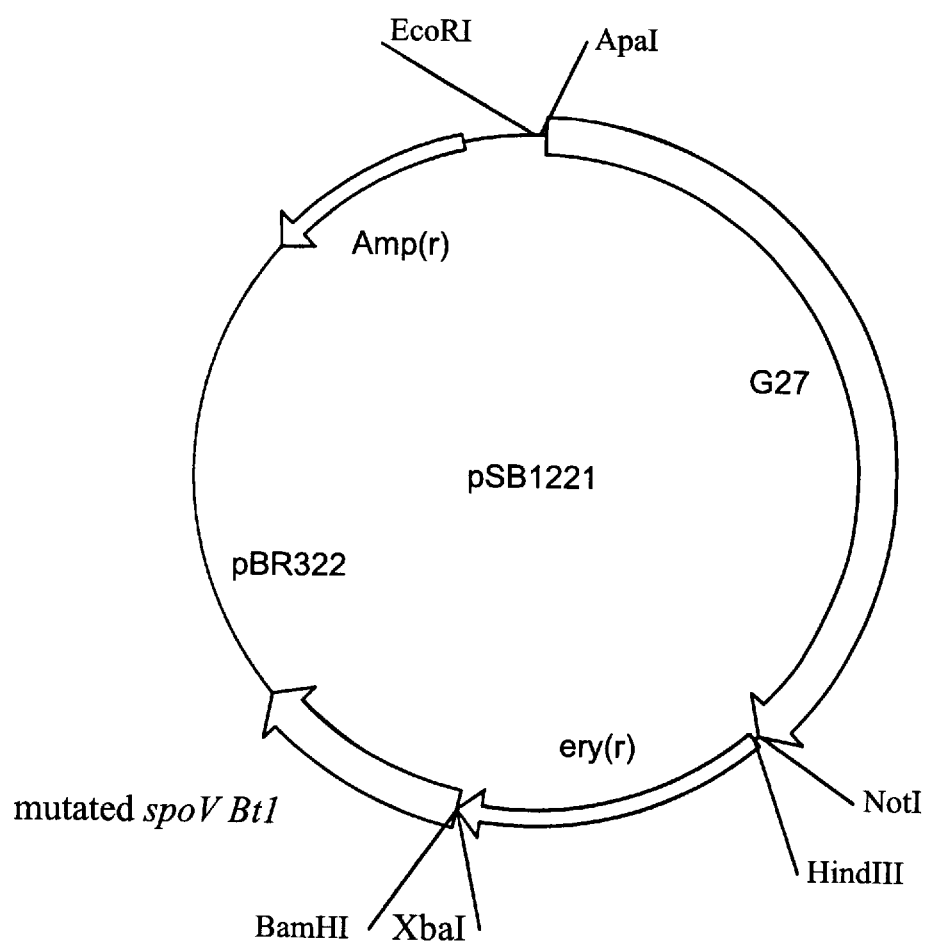
FIG. 15 illustrates plasmid pSB1221.

The G27 is isolated from pSB458 using ApaI and NotI digests and ligated to pSB1219 at the ApaI/NotI sites. The resulting plasmid is called pSB1221 (FIG. 15). This plasmid is used for integrating G27 by the transformation process described below into B. thuringiensis chromosome at the homologous spoVBt1 region while creating a mutation at the site.

Other crystal genes are also cloned at the ApaI and NotI sites of pSB1219 and pSB1220 and then integrated into the *B. thuringiensis* chromosome at the homologous spoVBt1 region while creating a mutation at that site.

D. *B. thuringiensis* Transformation.

To prepare competent HD73 and W4D23 *B. thuringiensis* cells, strains are grown in 50 ml BHIS medium (50% brain heart infusion broth, 50% 1M sucrose) at 37° C. and 300 rpm until they reach $OD_{600}$ of 0.2–0.3. W4D23 is a crystal-minus derivative of HD73. The cells are washed successively in one volume, ½ volume, and ¼th volume of ice-cold HEPES/sucrose solution. The cells are finally resuspended in 1/20th volume of HEPES/sucrose solution. *B. thuringiensis* competent cells (40 μl for 0.1 cm curvette and 200 μl for 0.2 cm curvette) are mixed with 5–20 μl of DNA (2–10 μg) in a prechilled electrode Gene Pulser Cuvette, and exposed to the electrical current in the Gene Pulser electroporation apparatus. The parameters for the electroporation are 0.9 kV, 3 μF and R=600 for 0.1 cm curvette and 1.25 kV, 3 μF, Ω=600 for the 0.2 cm curvette. The cells are immediately transferred to 400 μl or 1.8 ml BHIS and grown at 37° C. for 4 hours at 250 rpm. During this period, the vector pSB1221 inserts into the chromosome via homologous recombination (a single cross-over) between the homologous spoVBt1 sequences on the bacterial chromosome and the integration vector. This results in the formation of two spoVBt1 genes, one on each side of the integrated DNA segment. After four hours of growth, the cells are transferred to LB agar plates containing the appropriate antibiotic. The plates are incubated overnight at 30° C. and the transformants are restreaked onto fresh plates. The colonies are screened by PCR to confirm the presence of the ermC gene using the primers PG2 and PG4 to amplify a 0.3 kb fragment. Integration of pSB1221 into the spoVBt1 chromosomal locus is proven by PCR amplication of a 1261 bp produced between the upstream portions of spoVBt1 not included in pSB1221 integration vector using primer MS12A and the pBR322 portion of pSB1221 using primer pBR4. Results indicate that crystal encoding proteins are incorporated in the *B. thuringiensis* chromosome.

| Primer | Sequence (5'-3') | SEQ ID NO. |
|---|---|---|
| PG2 | GAAATCGGCTCAGGAAAAGG | 35 |
| PG4 | AGCAAACCCGTATTCCACG | 36 |
| PBR4 | GCACGATCATGCGCACCC | 37 |

Mutant spores resulting from integration of pSB1221 did not revert to wild type and spontaneously degraded within two weeks after growth when stored in liquid or on solid bacterial media.

Example 3

Generalized Transduction to Move the Integrated DNA to Alternative *B. thuringiensis* Hosts.

Integration occurs through homologous recombination (a double cross-over event) between DNA segments on both sides of the integrated vector in the donor strain and their homologous regions on the chromosome of the recipient strain. The donor strain containing the integrated vector is grown in 10 ml LB $Ery^5$ plate at 30° C. overnight (16–18 hours). Approximately one hundred microliters of the overnight culture are used to inoculate 10 ml LB containing 0.4% glycerol. The culture is then incubated at 30° C. and 300 rpm to an $OD_{600}$ of 1–2. To infect the cells with the phage CP-51ts45, (obtained from Dr. Curtis B. Thorne, University of Massachusetts at Amherst), different amounts of the phage lysate, $1\times10^5$ to $5\times10^6$ plaque forming units (PFU), are added to $2\times10^7$ cells in 3 ml Phage Assay (PA) soft agar (0.8% nutrient broth, 0.5% NaCl, 0.02% $MgSO_4.7H_2O$, 0.005% $MnSO_4.H_2O$, 0.015% $CaCl_2.2H_2O$, pH 6.0, 0.5% Bacto Agar) which is previously equilibrated at 50° C. The mixtures are then poured onto PA plates (PA medium containing 1.5% Bacto Agar), allowed to solidify, and incubated at 30° C. for 16 hours. The top agar, which contains hundreds of plaques in a lawn of cells, is collected in 3 to 6 ml of PA medium. The phage lysate is maintained at 16° C. for 3–4 hours, centrifuged (4,000×g, 5 minutes, 16° C.), and the supernatant is filter-sterilized using a 0.45 μM filter (VWR Scientific). The phage lysate is stored at 16° C. for long term storage. The titer of the phage lysate is approximately $1\times10^9$ to $1\times10^{10}$ PFU/ml.

For generalized transduction, the G27 insecticidal gene, erythromycin marker gene and (m) spoVBt1-8 are moved into the unmutated spoVBt1 chromosomal locus of a *Bt kurstaki* strain which normally contains cryIA(c), IA(b) and IA(c) genes. The recipient strain is grown in 10 ml LB at 30° C. for 16–18 hours. Two hundred milliliters of LB are inoculated with 2–3 ml of the overnight culture and grown at 30° C. and 300 rpm to an $OD_{600}$ of 1. The cells are centrifuged (7,520×g, 4° C., 15 minutes) and resuspended in LB at a concentration of approximately $2\times10^9$ colony forming units (CFU)/ml (approximately 100 fold concentrated). The transduction mixture, which contains $8\times10^8$ recipient cells and $4.9\times10^8$ to $8\times10^8$ PFU from the phage lysate, is incubated at 37° C. and 250 rpm for 30 minutes. The cell/phage suspension is spread on HA Millipore membranes (Millipore Corporation, Bedford, Mass.), placed on LB plates containing $Ery^{0.15}$, and incubated at 37° C. for 3–4 hours. The membranes are then transferred to LB plates containing $Ery^5$ and incubated at 37° C. for 18–20 hours.

The transduced isolates are confirmed using PCR as described above and microscopic viewing of the altered spore phenotype. The amount of protein in each isolate is determined using SDS Page as well as bioassay against *T. ni* and *S. exigua*. Isolates showed production of the 135 Kdalton insecticidal crystal protein.

What is claimed:

1. An isolated spoV DNA sequence selected from the group consisting of
   i) a spoVbt1 gene having the nucleotide sequence depicted in SEQ ID NO.1;
   ii) a nucleotide sequence encoding a *Bacillus thuringiensis* sporulation protein as depicted in SEQ ID NO.2;
   iii) a nucleotide sequence which hybridizes to a complementary strand of a sequence of i) or ii) under stringent hybridization conditions and
   iv) a truncated nucleotide sequence of i), ii) or iii) above wherein said truncated sequence includes at least 500 nucleotides.

2. An isolated spoV DNA sequence according to claim 1 wherein said sequence is a truncated nucleotide sequence of the spoVBt1 gene having the nucleotide sequence depicted in SEQ ID No.1.

3. An isolated spoV DNA sequence according to claim 1 wherein the sequence is a nucleotide sequence encoding a *Bacillus thuringiensis* sporulation protein as depicted in SEQ ID No:2.

4. A DNA segment comprising the spoV DNA sequence according to claim 1 and DNA sequences encoding at least one insecticidal crystal protein.

5. The DNA segment according to claim 4 further comprising an origin of replication from a gram negative bacterium and a selectable marker.

6. The DNA segment according to claim 4 wherein said crystal protein encoding sequence is selected from the group consisting of cryIA(a), cryIA(b), cryIA(c), cryIB, cryIC, cryID, cryIE, cryIF, cryIG, cryIH, cryIIA, cryIIb, cryIIIA, cryIIIB, cryIIIC, cryIVA, cryIVB, cryIVC, cryIVD, cryV genes, mixtures thereof and sequences constructed from parts of these cry genes.

7. The DNA segment according to claim 4 wherein the DNA sequence encodes a hybrid toxin protein wherein said hybrid protein comprises domains of two or three different crystal encoding toxins.

8. The DNA segment according to claim 7 wherein said hybrid protein includes domain III of cryIC.

9. A vector comprising the DNA segment of claim 4.

10. A *Bacillus thuringiensis* host transformed with the DNA segment of claim 4.

11. The progeny of the transformed host of claim 10.

12. A method of preparing a transformed *Bacillus thuringiensis* host expressing one to three exogenous crystal protein encoding genes comprising
   a) obtaining a DNA segment according to claim 4;
   b) introducing said segment into a *Bacillus thuringiensis* host;
   c) allowing homologous recombination between the DNA segment and a substantially homologous nucleotide fragment of a sporulation gene in the host *Bacillus thuringiensis* chromosome wherein the DNA segment is stably integrated into the *Bacillus thuringiensis* host chromosome; and
   d) isolating stably transformed *Bacillus thuringiensis* transformants
wherein said stable transformed *Bacillus thuringiensis* is capable of producing the exogenous crystal protein.

13. The transformed *Bacillus thuringiensis* host of claim 12.

14. An insecticidal composition comprising an insecticidally effective amount of the *Bacillus thuringiensis* host of claim 11.

15. An isolated mutated spoV DNA sequence selected from the group consisting of
   i) the nucleotide sequence of SEQ ID NO.1;
   ii) a nucleotide sequence encoding a *Bacillus thuringiensis* sporulation protein as depicted in SEQ ID NO.2;
   iii) a nucleotide sequence which hybridizes to a complementary strand of a sequence of i) or ii) under stringent hybridization conditions and
   iv) a truncated nucleotide sequence of i), ii) or iii) above wherein said truncated sequence includes at least 300 nucleotides,
wherein the nucleotide sequence of i), ii), iii) or iv) above has one or more point mutations, inserts or deletions, wherein the point mutation, insert or deletion creates a stop codon.

16. A mutated spoV DNA sequence according to claim 15 wherein the sequence is a mutated sequence of SEQ ID NO.1 and said mutation consists or between one to twenty-five point mutations before nucleotide number 1404, wherein each point mutation creates a stop codon.

17. A mutated spoV DNA sequence according to claim 15 wherein the sequence is a truncated mutated nucleotide sequence comprising base pair 465 through 1265 of SEQ ID NO.1 and said point mutations are between one and twenty-five, wherein each point mutation creates a stop codon.

18. A DNA segment comprising the mutated spoV DNA of claim 15 and one to three insecticidal crystal protein encoding genes.

19. The DNA segment according to claim 18 wherein said crystal protein encoding gene is selected from the group consisting of cryIA(a), cryIA(b), cryIA(c), cryIB, cryIC, cryID, cryIE, cryIF, cryIG, cryIH, cryIIA, cryIIb, cryIIIA, cryIIIB, cryIIIC, cryIVA, cryIVB, cryIVC, cryIVD, cryV genes, mixtures thereof and sequences constructed from parts of these cry genes.

20. The DNA segment according to claim 18 wherein the DNA sequence encodes a hybrid protein wherein said hybrid protein comprises domains of two or three different crystal encoding toxins.

21. A DNA segment comprising, the mutated spoV DNA sequence of claim 15, a crystal protein encoding gene and an origin of replication from a gram negative bacterium.

22. A method of preparing insecticidal crystal protein producing *Bacillus thuringiensis* strains with mutant spores comprising
   a) obtaining a DNA segment according to claim 21;
   b) introducing said segment into a sporulating *Bacillus thuringiensis* host;
   c) allowing homologous recombination to occur between the DNA segment and a substantially homologous sporulation gene fragment in the host *Bacillus thuringiensis* chromosome wherein said DNA segment including the mutated spoV DNA sequence is stably integrated into the *Bacillus thuringiensis* host chromosome; and
   d) isolating stably transformed *Bacillus thuringiensis* transformants
wherein said stable transformed *Bacillus thuringiensis* produces mutant spores and is capable of producing the exogenous crystal toxin proteins.

23. The method of claim 22 wherein said transformed *Bacillus thuringiensis* host is a *Bacillus thuringiensis kurstaki* strain.

24. The method of claim 22 wherein a substantially homologous sporulation gene fragment in the host chromosome is a spoVBt1 chromosomal fragment.

25. The transformed *Bacillus thuringiensis* host produced according to claim 22.

26. An insecticidal composition comprising an insecticidally effective amount of the *Bacillus thuringiensis* of claim 25.

27. A method according to claim 12 further comprising transducing the transformed *Bacillus thuringiensis* host comprising;
   a) exposing the *Bacillus thuringiensis* host to a transducing phage;
   b) allowing the phage to replicate in the host *Bacillus thuringiensis* wherein one to three exogenous crystal protein encoding DNA sequences integrated in the host chromosome are incorporated into the phage; and
   c) introducing the exogenous crystal protein encoding DNA sequences from the phage into a recipient *Bacillus thuringiensis*
wherein said introduced exogenous crystal protein encoding DNA sequence is stably incorporated into the recipient *Bacillus thuringiensis* chromosome and expressed in said recipient.

28. A method according to claim 22 further comprising transducing the transformed *Bacillus thuringiensis* host comprising;
   a) exposing the *Bacillus thuringiensis* host to a transducing phage;
   b) allowing the phage to replicate in the host *Bacillus thuringiensis* wherein the mutated spoV DNA sequence and one to three exogenous crystal protein encoding DNA proteins integrated in the host chromosome are incorporated into the phage; and
   c) introducing the exogenous crystal toxin encoding DNA sequences from the phage into a recipient *Bacillus thuringiensis*
wherein the mutated spoV DNA sequence and said exogenous crystal protein encoding DNA sequence proteins are stably incorporated into the recipient *Bacillus thuringiensis* chromosome and the exogenous crystal protein is expressed in said recipient wherein the recipient produces mutant spores.

29. A method according to claim 28 wherein said mutated spoV DNA sequence and exogenous crystal protein encoding DNA sequence are incorporated at a sporulation gene chromosomal fragment.

30. A method according to claim 29 wherein the recipient is a strain of *Bacillus thuringiensis kurstaki*.

31. A method according to claim 29 wherein the DNA segment comprises a truncated mutated spoV DNA sequence including nucleotide sequence 465 to 1256 of SEQ ID No.1 with one to twenty-five point mutations and wherein the crystal toxin encoding DNA is cryIA(b), cryIA(c), cryIC, cryIIA or cryIE and sequences constructed from parts thereof.

32. The transduced strain of claim 29.

33. An insecticidal composition comprising an insecticidally effective amount of the strain of claim 32.

34. A method of using a *Bacillus thuringiensis* chromosomal sporulation gene, or fragment thereof, as a locus for chromosomal integration of a DNA segment, said segment comprising one to three insecticidal crystal protein encoding genes wherein said gene is stably integrated into the *Bacillus thuringiensis* chromosome, wherein said sporulation gene, or fragment thereof, is selected from the group consisting of:
   i) the nucleotide sequence of SEQ ID NO.1;
   ii) a nucleotide sequence encoding a *Bacillus thuringiensis* sporulation protein as depicted in SEQ ID NO.2;
   iii) a nucleotide sequence which hybridizes to a complementary strand of a sequence of i) or ii) under stringent hybridization conditions;
   iv) a truncated nucleotide sequence of i), ii), or iii) above wherein said truncated sequence includes at least 300 nucleotides; or
   v) the nucleotide sequence of i), ii), iii), or iv) above which has one or more point mutations, inserts, or deletions, wherein the point mutation, insert or deletion creates a stop codon.

35. A method according to claim 34 wherein the Bacillus is a strain of *Bacillus thuringiensis kurstaki*.

36. A method according to claim 34 wherein the stable integration renders the *Bacillus thuringiensis* and any progeny thereof an oligosporogenic or asporogenic strain.

37. An isolated spoV DNA sequence according to claim 1 wherein the sequence is the spoVBt1 gene having the nucleotide sequence depicted in SEQ ID No.1.

38. An isolated spoV DNA sequence according to claim 2 wherein said truncated nucleotide sequence of SEQ ID No.1 includes the nucleotides from position 488 through 1404.

* * * * *